United States Patent
Wu

(10) Patent No.: US 8,871,079 B2
(45) Date of Patent: *Oct. 28, 2014

(54) VOLTAMMETRIC SYSTEMS FOR ASSAYING BIOLOGICAL ANALYTES

(75) Inventor: Huan-Ping Wu, Granger, IN (US)

(73) Assignee: Bayer HealthCare LLC, Whippany, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/611,557

(22) Filed: Sep. 12, 2012

(65) Prior Publication Data

US 2013/0240377 A1    Sep. 19, 2013

Related U.S. Application Data

(62) Division of application No. 11/596,309, filed as application No. PCT/US2005/017009 on May 16, 2005, now Pat. No. 8,287,717.

(60) Provisional application No. 60/571,388, filed on May 14, 2004.

(51) Int. Cl.
  *G01N 27/49* (2006.01)
  *G01N 27/327* (2006.01)

(52) U.S. Cl.
  CPC ..................... *G01N 27/49* (2013.01); *G01N 27/327* (2013.01)
  USPC ... 205/777.5; 205/792; 205/779; 204/403.01; 422/82.01; 435/287.1; 435/14

(58) Field of Classification Search
  USPC ............. 204/403.01–403.15; 205/777.5, 778, 205/792; 422/82.01, 68.1; 435/287.1, 14
  See application file for complete search history.

(56) References Cited

U.S. PATENT DOCUMENTS

| | | | | |
|---|---|---|---|---|
| 4,340,458 A | * | 7/1982 | Lerner et al. | 204/406 |
| 4,528,270 A | * | 7/1985 | Matsunaga | 205/777.5 |
| 4,897,162 A | | 1/1990 | Lewandowski et al. | |
| 5,108,564 A | | 4/1992 | Szuminsky et al. | |
| 5,120,420 A | | 6/1992 | Nankai et al. | |
| 5,124,011 A | | 6/1992 | Rogers et al. | |
| 5,403,451 A | | 4/1995 | Riviello et al. | |
| 5,429,735 A | | 7/1995 | Johnson et al. | |

(Continued)

FOREIGN PATENT DOCUMENTS

| CN | 1156573 | 6/2004 |
|---|---|---|
| EP | 1143240 | 10/2001 |

(Continued)

OTHER PUBLICATIONS

Polar 3.2 for Windows 1999.*
IP Australia, "Examination Report ", Feb. 5, 2008, Published in: Australia.

(Continued)

*Primary Examiner* — Jennifer Dieterle
(74) *Attorney, Agent, or Firm* — Blanchard & Associates

(57) ABSTRACT

The present invention relates to systems, methods, and devices for determining the concentration of an analyte in a sample. The use of linear, cyclic, or acyclic voltammetric scans and/or semi-integral, derivative, or semi-derivative data treatment may provide for increased accuracy when determining the concentration of an analyte in a sample. Hematocrit compensation in combination with the data treatments may reduce the hematocrit effect with regard to a glucose analysis in whole blood.

In another aspect, fast scan rates may reduce the hematocrit effect.

29 Claims, 29 Drawing Sheets

(56) References Cited

U.S. PATENT DOCUMENTS

| | | | |
|---|---|---|---|
| 5,508,171 | A | 4/1996 | Walling et al. |
| 5,620,579 | A | 4/1997 | Genshaw et al. |
| 5,628,890 | A | 5/1997 | Carter et al. |
| 5,645,710 | A | 7/1997 | Shieh |
| 5,650,061 | A | 7/1997 | Kuhr et al. |
| 5,653,863 | A | 8/1997 | Genshaw et al. |
| 5,708,247 | A | 1/1998 | McAleer et al. |
| 5,798,031 | A | 8/1998 | Charlton et al. |
| 5,873,990 | A | 2/1999 | Wojciechowski et al. |
| 5,942,102 | A | 8/1999 | Hodges et al. |
| 5,951,836 | A | 9/1999 | McAleer et al. |
| 5,958,215 | A | 9/1999 | Kuhr et al. |
| 6,120,676 | A | 9/2000 | Heller et al. |
| 6,153,069 | A | 11/2000 | Pottgen et al. |
| 6,258,254 | B1 | 7/2001 | Miyamoto et al. |
| 6,387,614 | B1 * | 5/2002 | Cheng et al. .................. 435/4 |
| 6,413,411 | B1 | 7/2002 | Pottgen et al. |
| 6,413,441 | B1 | 7/2002 | Levin |
| 6,458,258 | B2 | 10/2002 | Taniike et al. |
| 6,475,372 | B1 * | 11/2002 | Ohara et al. ............... 205/777.5 |
| 6,531,040 | B2 | 3/2003 | Musho et al. |
| 6,576,101 | B1 | 6/2003 | Heller et al. |
| 6,576,117 | B1 | 6/2003 | Iketaki et al. |
| 6,592,745 | B1 | 7/2003 | Feldmen et al. |
| 6,628,890 | B1 | 9/2003 | Yamamoto et al. |
| 6,689,365 | B1 | 2/2004 | Boime |
| 6,824,669 | B1 | 11/2004 | Li et al. |
| 2002/0180446 | A1 * | 12/2002 | Kuhr et al. ................... 324/432 |
| 2003/0111993 | A1 | 6/2003 | Olofsson |
| 2003/0119208 | A1 | 6/2003 | Yoon et al. |
| 2003/0136673 | A1 | 7/2003 | Pilloud et al. |
| 2003/0201194 | A1 * | 10/2003 | Heller et al. .............. 205/777.5 |

FOREIGN PATENT DOCUMENTS

| | | |
|---|---|---|
| JP | 63171357 | 7/1988 |
| JP | 1003554 | 1/1989 |
| JP | 4118554 | 4/1992 |
| JP | 08247994 | 9/1996 |
| JP | 2001311712 | 11/2001 |
| WO | 9913325 | 3/1999 |
| WO | 0133206 | 5/2001 |
| WO | 0157510 | 8/2001 |
| WO | 0218627 | 3/2002 |
| WO | 2005114164 | 12/2005 |

OTHER PUBLICATIONS

State Intellectual Property Office, P.R. China, "First Office Action", Apr. 24, 2009, Published in: China.

EPO, "Search Report and Written Opionion for PCT/US2005/017009", Dec. 6, 2005, Publisher: International Searching Authority.

Intellectual Property Office of New Zealand, "Examination Report", Apr. 9, 2008, Published in: New Zealand.

Russian Agency for Patents and Trademarks, "Official Action", Apr. 9, 2009, Published in: Russia.

Intellectual Property Office of Singapore, "Written Opinion", Nov. 12, 2007, Published in: Singapore.

Bard, et al., "Electrochemical Methods Fundmentals and Application", 1980, pp. 236-241.

Dalrymple-Alford, P., et al., "Peak Shapes in Semi-differential Electroanalysis", "Anal. Chem.", 1977, pp. 1390-1394, vol. 49, No. 9, Publisher: American Chemical Society, Published in: USA.

Fung, Y S, et al., "Application of Dual-Pulse Staircase Voltammetry for Simultaneous Determination of Glucose and Fructose", "Electroanalysis", 1995, pp. 160-165, vol. 7, No. 2, Publisher: VHC Publishers, Inc. US, Published in: Department of Chemistry, University of Hong Kong, Hong Kong.

Goto, et al., "Semi-integral Electroanalysis: Shapes of Neopolarograms", "Anal Chem.", 1973, p. 2043 vol. 45.

Klicka, et al., "Adsorption in Semi-Differential Voltammetry", 1998, p. 253 vol. 455.

Oldham, K.B, "A Signal-Independent Electroanalytical Method", 1972, p. 196 vol. 44, Publisher: Anal. Chem.

Oldham, "Convolution: A General Electrochemical Procedure Implemented by a Universal Algorithm", "Anal Chem.", 1986, p. 2296 vol. 58.

Pedrosa, J.M., et al., "Application of the Cyclic Semi-Integral Voltammetry and Cyclic Semi-Differential Voltammetry to the Determination . . . ", "J. Electroanal. Chem.", 2002, p. 160 vol. 523, Publisher: American Chemical Society, Published in: USA.

Sanchez-Maestre, M. et al., "The cyclic voltammetric behaviour of 4,4-bipyridine over mercury in an acid medium", "Electrochimica Acta.", 1996, pp. 819-825, vol. 41, No. 6.

Yu, et al., "Differentiation, semidifferentiation and semi-integration of a digital signals based on Fourier transformation", "Journal of Electroanalytical Chemistry", 1996, pp. 1-9, vol. 403.

Kumar, et al., "Electrochemical Investigation of Glucose Sensor Fabricated at Copper-Plated Screen-Printed Carbon Electrodes", "Electroanalysis", 2002, pp. 671-678, vol. 14, No. 10.

* cited by examiner

VOLTAMMETRIC SYSTEMS FOR ASSAYING BIOLOGICAL ANALYTES

REFERENCE TO RELATED APPLICATIONS

This application is a division of U.S. Nonprovisional application Ser. No. 11/596,309, entitled "Voltammetric Systems for Assaying Biological Analytes," having a 371(c) date of Sep. 7, 2007, which is the National Stage of International Application No. PCT/US05/17009, entitled "Voltammetric Systems for Assaying Biological Analytes," which was filed May 16, 2005, and which claimed the benefit of U.S. Provisional Application No. 60/571,388, entitled "Methods for Using Linear or Cyclic Voltammetry in Assaying Glucose and Other Biological Analytes," filed May 14, 2004, each of which is incorporated by reference in its entirety.

BACKGROUND

The quantitative determination of analytes in biological fluids is useful in the diagnosis and treatment of physiological abnormalities. For example, determining the glucose level in biological fluids, such as blood, is important to diabetic individuals who must frequently check their blood glucose level to regulate their diets and/or medication.

Electrochemical methods have been used for such purposes. An electrochemical biosensor may use an analyte specific enzyme, such as glucose oxidase or glucose dehydrogenase, to catalyze the oxidation of glucose in a whole blood sample. During the catalytic oxidation by the enzyme, the redox center of the enzyme accepts the electrons from the analyte.

This redox center could be the flavin adenine dinucleotide (FAD) of glucose oxidase, or the enzyme's cofactor such as pyrroloquinoline quinone (PQQ) for the glucose dehydrogenase. The electrons acquired by the enzyme then may be moved to the electrode by a mediator, which is converted to a reduced form through oxidation of the enzyme. Finally, the reduced form of the mediator, such as the ferrocyanide species of the ferricyanide/ferrocyanide redox pair, is oxidized at the electrode to generate a measurable current.

This process may be represented by the following equations:

$$\text{Glucose} + E_{Ox} = E_{Red} + \text{Product} \quad (1)$$

$$E_{Red} + n\text{Med}_{Ox} = n\text{Med}_{Red} + E_{Ox} \quad (2)$$

$$\text{Med}_{Red} = \text{Med}_{Ox} + ne^- \quad (3)$$

where $E_{Ox}$ and $E_{Red}$ are the oxidized and reduced forms of the redox center of the enzyme, respectively, while $\text{Med}_{Ox}$ and $\text{Med}_{Red}$ are the oxidized and reduced forms of the mediator, respectively. The product of the enzymatic reaction may be gluconic acid or gluconolactone.

One electrochemical method, which has been used to quantify analytes in biological fluids, is coulometry. For example, Heller et al. described the coulometric method for whole blood glucose measurements in U.S. Pat. No. 6,120,676. In coulometry, the analyte (glucose) concentration is quantified by exhaustively oxidizing the analyte within a small volume and integrating the current over the time of oxidation to produce the electrical charge representing the analyte concentration. In other words, coulometry captures the total amount of glucose within the sensor strip.

An important aspect of coulometry is that towards the end of the integration curve of charge vs. time, the rate at which the charge changes becomes relatively constant to yield a steady-state condition. This steady-state portion of the coulometric curve forms a relatively flat plateau region in the curve, thus allowing accurate determination of the corresponding current. However, the coulometric method requires the complete conversion of the entire volume of analyte. As a result, this method is time consuming and does not provide the fast results which users of electrochemical devices, such as glucose-monitoring products, demand. Another problem with coulometry is that the small volume of the sensor cell must be controlled in order to provide accurate results, which can be difficult with a mass produced device.

Another electrochemical method which has been used to quantify analytes in biological fluids is amperometry. In amperometry, current is measured at the end of a period at a constant potential (voltage) across the working and counter electrodes of the sensor strip. The current is used to quantify the analyte in the biological sample. Amperometry measures the rate at which the electrochemically active species, and thus the analyte, is being oxidized or reduced. Many variations of the amperometric method for biosensors have been described, for example in U.S. Pat. Nos. 5,620,579; 5,653,863; 6,153,069; and 6,413,411. The amperometric method samples the analyte concentration near the electrode surface by measuring the current that is proportional to the diffusion rate and the bulk concentration of the analyte.

A disadvantage of the amperometric method is the non-steady-state nature of the current after applying a potential. The rate of current change with respect to time is very fast initially and becomes slower as the analysis proceeds due to the changing nature of the underlying diffusion process. Until the consumption rate of the reduced mediator at the electrode surface equals the diffusion rate, a steady-state current cannot be obtained. Thus, measuring a current during a non-steady-state time period may be associated with more inaccuracy than a measurement taken at a steady-state time period.

One important aspect of measuring analytes in whole blood samples is the effect of hematocrit. Hematocrit is the volume of red blood cells (RBC) expressed as a percentage of the volume of RBC in a whole blood sample. The hematocrit value for whole blood samples ranges from about 20 to 60% and is typically about 40%.

Reagent biosensors include any system that can detect glucose in a blood specimen via an electrochemical reaction. Examples of reagent biosensors include Ascensia AUTO-DISC® and Elite® biosensors available from Bayer HealthCare, LLC of Elkhart, Ind.; Precision® biosensors available from Abbott in Abbott Park, Ill.; Accucheck® biosensors available from Roche in Indianapolis, Ind.; and OneTouch Ultra® biosensors available from Lifescan in Milpitas, Calif.

Typical electrochemical sensor strips contain a working electrode, a counter electrode, and an optional third electrode. A reference potential may be provided to the system by the counter electrode, if configured appropriately, or by the optional third electrode. A reagent layer with an enzyme such as glucose oxidase or glucose dehydrogenase and a mediator such as ferricyanide or ruthenium hexaamine is printed or deposited onto the working electrode or onto the working and counter electrodes with a polymer as the binder.

Examples of polymers used as the binder of the reagents include CMC (carboxyl methyl cellulose) and PEO (polyethylene oxide). The addition of various types and molecular weights of polymers to the reagent layer may assist in filtering red blood cells, preventing them from coating the electrode surface.

Preferably, the sensor strip is made by printing electrodes on an insulating substrate using multiple techniques, such as those described in U.S. Pat. Nos. 6,531,040; 5,798,031; and 5,120,420. The reagent can be co-printed onto the working and counter electrodes with a mixture of a glucose oxidizing enzyme such as glucose oxidase, a mediator such as ferricyanide, a hydrophilic polymer such as polyethylene oxide (PEO) and an appropriate buffer, such as a citrate buffer.

Alternatively, a different reagent chemistry can be either printed or micro-deposited separately onto the working and counter electrodes using the method described in a U.S. provisional patent application filed Oct. 24, 2003, Ser. No. 60/513,817 with the reagent on the working electrode containing the enzyme, the mediator, the polymer and that on the counter electrode containing a soluble redox species, which could be the same as the mediator or different, and a polymer. In one embodiment, the polymer used in micro-deposition is carboxyl methyl cellulose.

Examples of suitable bench-top electrochemical instruments which may be used for reading reagent biosensors according to the present invention include, but are not limited to, the BAS 100B Analyzer available from BAS Instruments in West Lafayette, Ind.; the CH Instrument Analyzer available from CH Instruments in Austin, Tex.; the Cypress Electrochemical Workstation available from Cypress Systems in Lawrence, Kans.; and the EG&G Electrochemical Instrument available from Princeton Research Instruments in Princeton, N.J. Examples of portable instruments include the Ascensia Breeze® and Elite® meters of Bayer Corporation.

A biosensor for glucose may have an enzyme and a mediator deposited on the electrodes. The ability of this sensor to measure glucose is affected as the RBC block the diffusion of the relevant reagents within the blood sample. Since the amperometric current is directly proportional to the diffusion of the reduced form of the mediator, the hematocrit will have a significant impact on the accuracy of the glucose measurements. Depending on the hematocrit level in a whole blood sample, the RBC cause a bias in the glucose readings.

Various methods and techniques have been proposed in an attempt to reduce the hematocrit effect of the whole blood on the resulting glucose measurements. For example, Ohara et al. in U.S. Pat. No. 6,475,372 disclosed a method of using the ratio of currents from a forward and a reverse potential pulse to compensate for the hematocrit effect in electrochemical glucose measurements. McAleer et al. in U.S. Pat. Nos. 5,708,247 and 5,951,836 disclosed a reagent formulation using silica particles to filter the RBC from the electrode surface, thus reducing the hematocrit effect. Carter et al. in U.S. Pat. No. 5,628,890 disclosed a method of using a wide spacing of the electrodes combined with mesh layers to distribute the blood sample for the hematocrit effect.

These conventional techniques for reducing the bias attributable to the hematocrit effect include (a) co-deposition of a polymer to minimize the hematocrit effect, (b) addition of various kinds of fused silica to enforce the filter effect for the polymer layer, (c) compensation coefficients based on the ratio of currents from a forward and a reverse potential pulse, and (d) self-compensation by utilizing the existing solution resistance of the whole blood samples. Although these methods may be useful, conventional glucose sensors continue to exhibit significant analytical bias attributable to the hematocrit effect. Thus, it would be desirable to provide systems for quantifying analytes in biological fluids, in particular the glucose content of whole blood, which reduces bias from the hematocrit effect.

SUMMARY

In one aspect, the invention provides a method of determining the concentration of an analyte in a sample that includes applying an acyclic scan to the sample and determining the concentration of the analyte in the sample.

In another aspect, the invention provides a handheld analyte measuring device, for determining the concentration of an analyte in a sample. The analyte measuring device includes an acyclic scanning measuring device adapted to receive a sensor strip. The acyclic scanning measuring device includes at least two device contacts in electrical communication with a display through electrical circuitry. The sensor strip includes at least first and second sensor strip contacts in electrical communication with a working electrode and a counter electrode through conductors, where a first reagent layer is on at least one of the electrodes and the first layer includes an oxidoreductase and at least one species of a redox pair. Both acyclic and linear scanning measurement devices are provided.

In another aspect, the invention provides a method of determining the concentration of an analyte in a sample that includes applying a voltammetric forward linear scan to the sample, measuring the resulting currents, applying a data treatment to the measured currents, and determining the concentration of the analyte in the sample.

In another aspect, the invention provides a handheld measuring device, for determining the concentration of an analyte in a sample, where the device is adapted to receive a sensor strip. The device includes contacts, at least one display, and electronic circuitry establishing electrical communication between the contacts and the display. The electronic circuitry comprises an electric charger and a processor in electrical communication, the processor in electrical communication with a computer readable storage medium comprising computer readable software code. The computer readable software code, when executed by the processor, causes the processor to implement semi-integral, derivative, and/or semi-derivative data treatment and/or voltammetric scanning.

In order to provide a clear and consistent understanding of the specification and claims, the following definitions are provided.

The term "mediator" is defined as a substance that may be oxidized or reduced and that may transfer one or more electrons. A mediator is a reagent in an electrochemical analysis and is not the analyte of interest, but provides for the indirect measurement of the analyte. In a simplistic system, the mediator undergoes a redox reaction in response to the oxidation or reduction of the analyte. The oxidized or reduced mediator then undergoes the opposite redox reaction at the working electrode and is regenerated to its original oxidation number.

The term "redox reaction" is defined as a chemical reaction between two species involving the transfer of at least one electron from a first species to a second species. Thus, a redox reaction includes an oxidation and a reduction. The oxidation half-cell of the reaction involves the loss of at least one electron by the first species, while the reduction half-cell involves the addition of at least one electron to the second species. The ionic charge of a species that is oxidized is made more positive by an amount equal to the number of electrons transferred. Likewise, the ionic charge of a species that is reduced is made less positive by an amount equal to the number of electrons transferred.

The terms "redox pair" are defined as two conjugate species of a chemical substance having different oxidation numbers. Reduction of the species having the higher oxidation number produces the species having the lower oxidation number. Alternatively, oxidation of the species having the lower oxidation number produces the species having the higher oxidation number.

The term "oxidation number" is defined as the formal ionic charge of a chemical species, such as an atom. A higher oxidation number, such as (III), is more positive, and a lower oxidation number, such as (II), is less positive.

The term "reversible redox pair" is defined as a pair of redox species where the separation between the forward and reverse scans of the semi-integral is at most 30 mV at the half-height of the $si_{ss}$ transition. For example, in FIG. 3B the forward and reverse semi-integral scans for the ferricyanide/ferrocyanide redox pair in addition to the $si_{ss}$ transition height are shown. At the line where the half-height $si_{ss}$ transition line intersects the forward and reverse scan lines the separation between the lines is 29 mV, establishing the reversibility of the ferricyanide/ferrocyanide redox pair at the depicted scan rate.

The term "quasi-reversible redox pair" is defined as a redox pair where the separation between the forward and reverse scans of the semi-integral is larger than 30 mV at the half-height of the $si_{ss}$ transition for the redox pair.

The term "steady-state" is defined as when the change in electrochemical current with respect to voltage is relatively constant, such as within ±10 or ±5%.

The term "reversing-point" is defined as the point in a cyclic or acyclic scan when the forward scan is stopped and the reverse scan is initiated.

The term "linear scan" is defined as a scan where the voltage is varied in a single "forward" direction at a fixed scan rate, such as from −0.5 V to +0.5 V to provide a 1.0 V scan range. A linear scan may be approximated by a series of incremental changes in potential. If the increments occur very close together in time, they correspond to a continuous linear scan. Thus, applying a change of potential approximating a linear change may be considered a linear scan.

The term "cyclic scan" is defined as a combination of a linear forward scan and a linear reverse scan where the scan range includes the oxidation and reduction peaks of a redox pair. For example, varying the potential in a cyclic manner from −0.5 V to +0.5 V and back to −0.5 V is an example of a cyclic scan for the ferricyanide/ferrocyanide redox pair as used in a glucose sensor, where both the oxidation and reduction peaks are included in the scan range.

The term "acyclic scan" is defined in one aspect as a scan including more of one forward or reverse current peak than the other current peak. For example, a scan including forward and reverse linear scans where the forward scan is started at a different voltage than where the reverse scan stops, such as from −0.5 V to +0.5 V and back to +0.25 V, is an example of an acyclic scan. In another example, an acyclic scan may start and end at substantially the same voltage when the scan is started at most ±20, ±10, or ±5 mV away from the formal potential $E^{o\prime}$ of the redox pair. In another aspect, an acyclic scan is defined as a scan including forward and reverse linear scans that substantially exclude the oxidation and reduction peaks of a redox pair. For example, the scan may begin, reverse, and end within the steady-state region of a redox pair, thus excluding the oxidation and reduction peaks of the pair.

The terms "fast scan" and "fast scan rate" are defined as a scan where the voltage is changed at a rate of at least 176 mV/sec. Preferable fast scan rates are rates greater than 200, 500, 1000, or 2000 mV/sec.

The terms "slow scan" and "slow scan rate" are defined as a scan where the voltage is changed at a rate of at most 175 mV/sec. Preferable slow scan rates are rates slower than 150, 100, 50, or 10 mV/sec.

The term "handheld device" is defined as a device that may be held in a human hand and is portable. An example of a handheld device is the measuring device accompanying Ascensia® Elite Blood Glucose Monitoring System, available from Bayer HealthCare, LLC, Elkhart, Ind.

The term "on" is defined as "above" and is relative to the orientation being described. For example, if a first element is deposited over at least a portion of a second element, the first element is said to be "deposited on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating can be described as "on" the first element. Thus, the use of the term "on" may or may not mean that the two elements being related are in physical contact with each other.

DETAILED DESCRIPTION

Figure 1A:
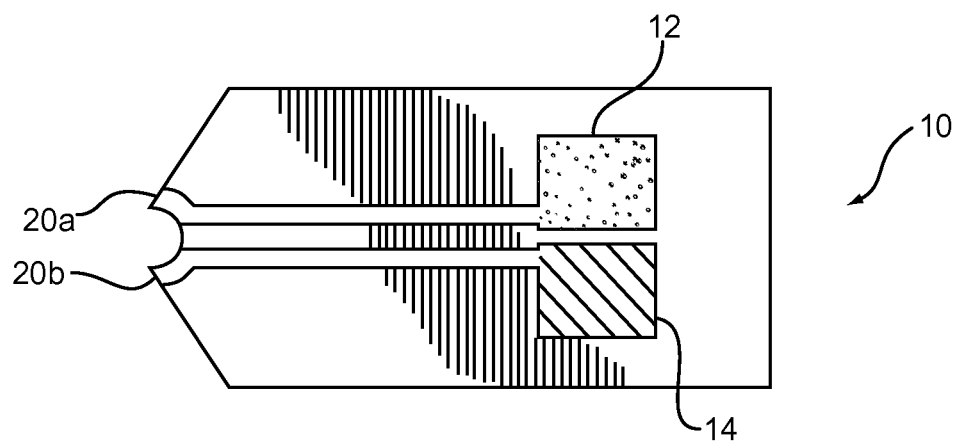
FIGS. 1A-1B depict top and end views of the working and counter electrodes of a typical sensor strip.

An electrochemical analytic system determines the concentration of analytes in biological fluids, such as the glucose concentration of whole blood. The system includes devices that may apply voltammetric linear, cyclic, or acyclic scans to a sensor strip containing a biological sample. Voltammetric scans measure currents (amperage) from a sensor strip while a potential (voltage) applied to the strip is varied linearly with time. The devices may compare the resulting current and voltage data to determine the concentration of the analyte in the sample, while correcting the results for variations in the hematocrit content of a specific blood sample. The devices also may apply one or more data treatments, including those based on semi-integration, derivatives, and semi-derivatives to compare and correct the voltammetric data.

The systems are generally described in the context of determining the concentration of glucose in a whole blood sample. However, the systems have other applications where analytes such as cholesterol, triglycerides, lactate, pyruvate, alcohol, bilirubin uric acid, NAD(P)H, and carbon monoxide are found in biological fluids including plasma, urine, saliva and interstitial fluid.

System Overview

The systems for determining analyte concentration may include a sensor strip for containing the sample and a measuring device for implementing one or more scanning technique and one or more data treatments. In one aspect, the invention may be a kit including one or more sensor strip and a handheld electronic device for implementing a scanning technique and a data treatment to output the concentration of the analyte.

The sensor strip may include a working electrode, a counter electrode, and optionally may include a reference or third electrode. In one aspect, the working and counter electrodes may be coated with a single layer of reagent by co-printing/co-deposition, such as in the Ascensia® AUTODISC sensor. In another aspect, each electrode may be coated with a reagent layer optimized for the electrode on which it resides. The reagent layer at the working electrode includes an enzyme which oxidizes the glucose in the blood sample and a mediator, such as a redox compound which re-oxidizes the enzyme after it has been reduced by oxidizing glucose. The reduced mediator, which carries electrons from the enzymatic reaction of the glucose oxidation to the electrode, is reoxidized at the surface of the working electrode.

This reoxidation results in the passing of electrons through the electrodes and the conductors of the sensor strip. The conductors of the sensor strip are in electrical communication with a measurement device, which applies a voltage differential between the electrodes. The device may record the current passing through the sensor as a measure of the glucose content of the blood sample.

A whole blood sample is applied to the sensor strip and the glucose in the blood reacts with the enzyme within or in close proximity to the reagent layer. The diffusion rate of the reduced mediator from the sample to the working electrode may limit the current passing between the working electrode and the counter electrode.

Scanning Techniques

Unlike conventional amperometry and coulometry where a constant voltage is applied while the current is measured as a function of time, voltammetry scanning involves applying a potential (Voltage) across the electrodes at a fixed rate (V/sec) and measuring the current as a function of the applied potential. Voltammetry scanning may be performed in a linear, cyclic, or acyclic manner. Cyclic voltammetry scanning is commonly referred to as "cyclic voltammetry."

During a linear scan the current at the working electrode is measured while the potential at the working electrode changes linearly with time at a constant rate. The scan range, such as from −0.5 V to +0.5 V, may cover the reduced and oxidized states of a redox pair so that a transition from one state to the other occurs. The current measured at the working electrode may be thought of as having three components: the equilibrium current, the diffusion current, and the surface current. The surface current, which may derive from any species adsorbed on the electrode, is generally small and may be neglected. The equilibrium and diffusion currents are the primary components represented in the resulting voltammogram.

A linear scan voltammogram (a plot of current verses voltage) may be characterized by a plot that starts at an equilibrium current, reaches a peak current, and decays to a lower current level during the scan. After the initial peak current, the measured current decays and approaches a steady-state region where the oxidation of the reduced mediator at the electrode surface reaches a maximum rate limited by diffusion. Thus, the steady-state current at this plateau region of the scan signifies the diffusion-limited current passing through the electrodes, which can be used as a measure of the glucose content of the blood sample.

After completion of the forward scan, for a cyclic or acyclic scan, a reversed potential linear scan is applied at substantially the same scan rate as the forward scan. Cyclic, and in some instances, acyclic scans may examine the transition of a redox species from a reduced state to an oxidized state (and vice versa) in relation to the applied potential or in relation to the diffusion rate of the redox species to the electrode surface.

In relation to a linear scan, cyclic and acyclic scans may provide a better representation of the steady-state (diffusion limited) portion of the scan. The advantage of cyclic and acyclic scans may be especially advantageous for quantifying the steady-state currents from quasi-reversible redox pairs at fast scan rates. Additional information about linear and cyclic scan voltammetry may be found in "Electrochemical Methods: Fundamentals and Applications" by A. J. Bard and L. R. Faulkner, 1980.

Acyclic scans may have multiple advantages over cyclic scans including a shorter scan time and a substantial decrease in the amount of mediator electrochemically converted to the measurable state. Thus, if the mediator is reduced in response to the analyte and electrochemically oxidized during measurement, terminating the reverse scan before the oxidized mediator is electrochemically reduced decreases the amount of reduced mediator in the sample not responsive to the analyte. Reducing the scan time may allow for a shorter analysis time, a significant benefit for the user.

Figure 3A:
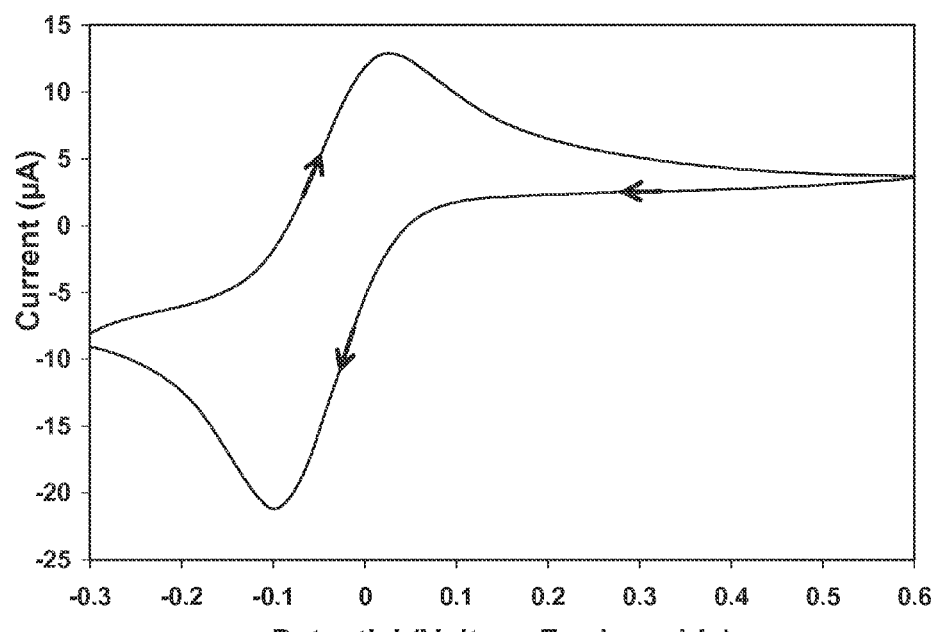
FIG. 3A is a graph showing a cyclic voltammogram from a sensor system.
Figure 3B:
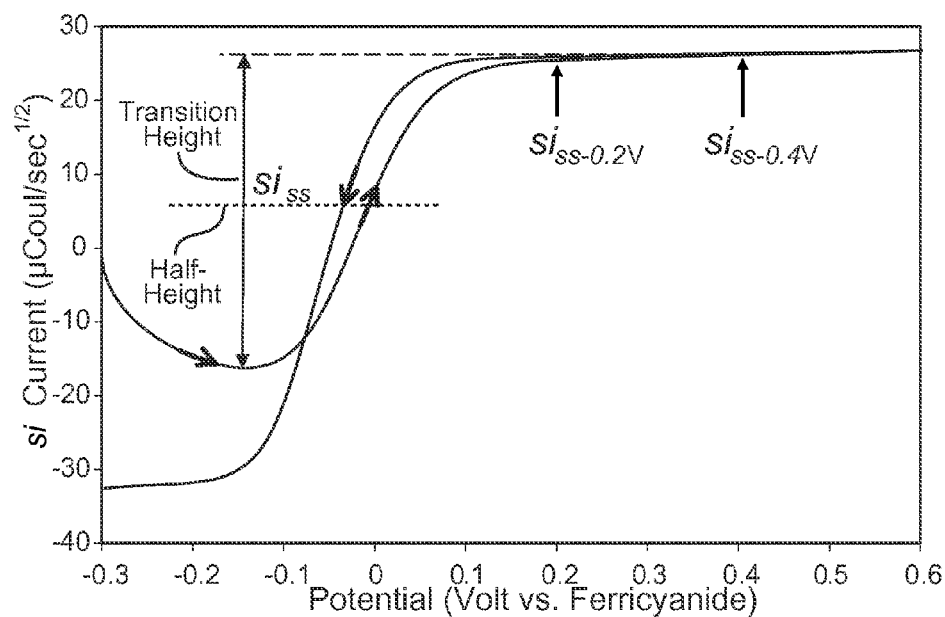
FIG. 3B is a graph of the semi-integral corresponding to the cyclic voltammogram of FIG. 3A.
Figure 3C:
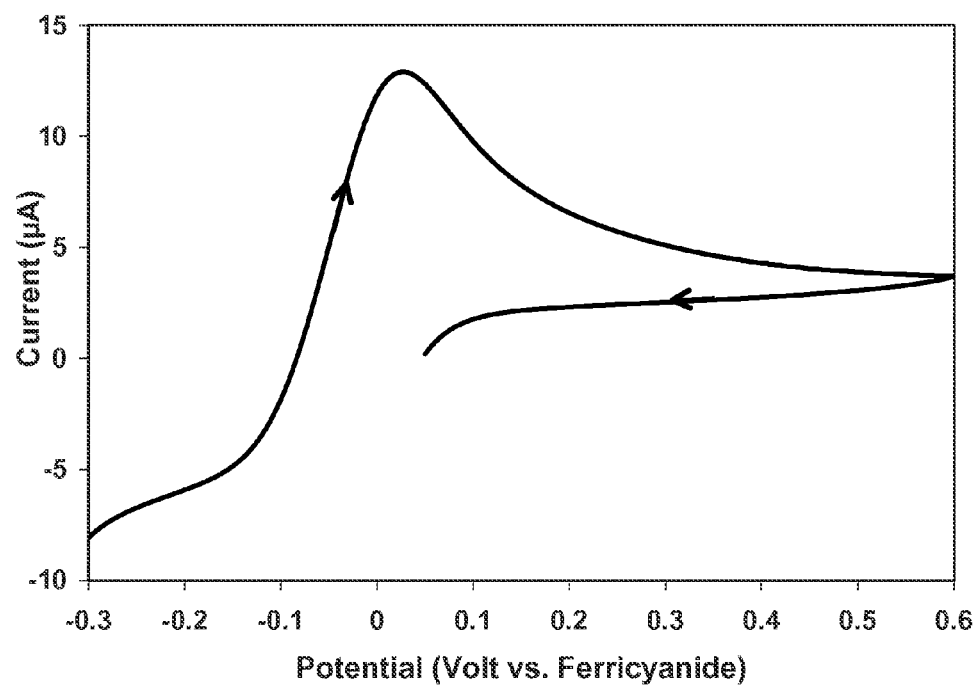
FIG. 3C shows an acyclic scan, where the reverse scan is terminated before initiation of the reverse current peak.
Figure 3D:
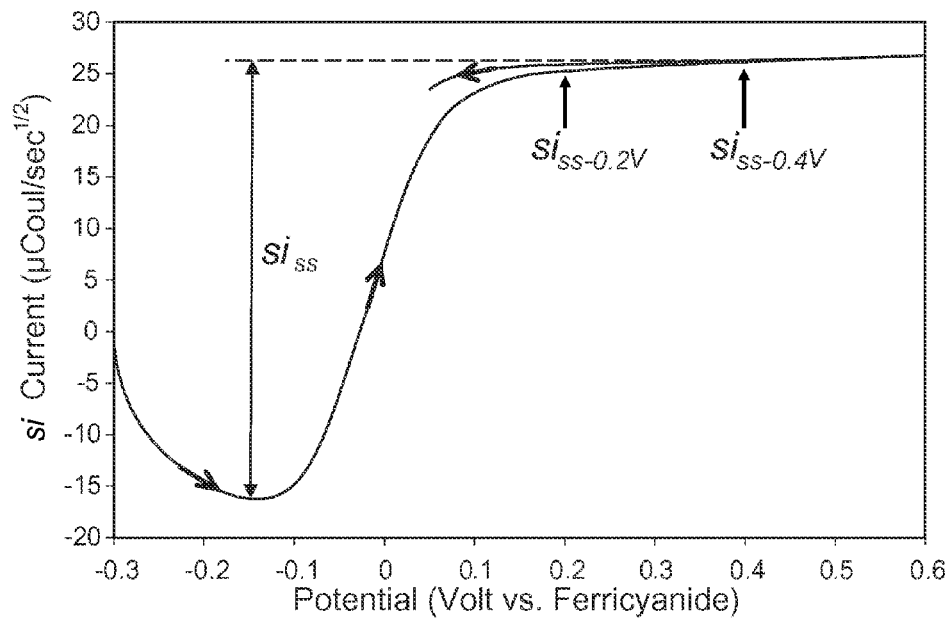
FIG. 3D presents the semi-integral of the acyclic data.

FIG. 3A presents the data from a 25 mV/sec cyclic scan of a ferricyanide/ferrocyanide redox pair as a cyclic voltammogram. The voltammogram is characterized by a forward scan peak during the positive voltage scan from −0.3 V to +0.6 V indicating ferrocyanide oxidation and a reverse scan peak during the negative voltage scan from +0.6 V back to −0.3 V indicating ferricyanide reduction. The forward and reverse scan peaks center around the formal potential $E^{0\prime}$ (−0.05 mV) of the ferrocyanide/ferricyanide redox pair, when referenced to the counter-electrode. In this aspect, the potential of the counter electrode is substantially determined by the reduction potential of ferricyanide, the major redox species present on the counter electrode. FIG. 3B presents the semi-integral of the voltammogram data to show the effect of this data treatment method on the raw data. FIG. 3C shows a comparable acyclic scan, where the reverse scan is terminated before initiation of the reverse current peak. FIG. 3D presents the semi-integral of the acyclic scan.

The scanning process leads to increasingly higher currents near the working electrode as the potential increases relative to the formal potential $E^{0\prime}$. At the same time, oxidation at the electrode surface generates a depleted area and thus a concentration gradient near the electrode. This concentration gradient creates a driving force for additional mediator to diffuse toward the electrode. In combination, these forces provide the initial forward peak in the voltammogram as the mediator reduced by the analyte or oxidoreductase travels to the working electrode and is reoxidized. As the scan continues, the current decays and approaches the steady-state region, from ~0.3 to ~0.6 V in FIG. 3A. The current measured in the steady-state region may be correlated with the concentration of the reduced mediator, and thus, the glucose content of the blood sample.

While the potentials where the forward and reverse scans begin (the scan range) may be selected to span the reduced and oxidized states of the redox pair, the scan range may be reduced to shorten the analysis time. However, the scan range preferably includes the steady-state region for the redox pair. For example, at a scan rate of 25 mV/sec, the concentration of the reduced [Red] and oxidized [Ox] species of the ferrocyanide/ferricyanide reversible redox pair and the resulting electrode potential are described by the Nernst equation as follows.

$$E = E^{0\prime} + \frac{RT}{nF}\ln\frac{[Ox]}{[Red]} \underline{T = 25° C.} E^{0\prime} + \frac{0.059}{n}\log\frac{[Ox]}{[Red]} \underline{n = 1} E^{0\prime} + 0.059\log\frac{[Ox]}{[Red]}$$

When the potential at the working electrode is referenced to its own redox potential, the formal potential $E^{0\prime}$ will become substantially zero and the equation collapses to:

$$E = 0.059\log\frac{[Ox]}{[Red]} = 0.059\log\frac{[Fe(CN)_6^{-3}]}{[Fe(CN)_6^{-4}]}. \quad (1)$$

From equation (1), when the ratio of the oxidized mediator to the reduced mediator changes by 10, the potential at the working electrode changes by about 60 mV. The reverse is also true. Thus, for ferricyanide [Ox] to ferrocyanide [Red] concentration ratios of 10:1, 100:1, 1000:1 and 10,000:1, the potential at the working electrode will be approximately 60, 120, 180, and 240 mV away from the zero potential, respectively.

Thus, when the ratio of ferricyanide to ferrocyanide is ~1000:1, a scan range of +180 mV to −180 mV would provide substantially complete oxidation of the reduced species at the working electrode. At 180 mV, the oxidation rate is limited by how fast the reduced form of the mediator can diffuse to the electrode surface, and from this potential forward, there exists a diffusion-limited steady-state current region. Thus, if the reversing point is set ~400 mV from the zero potential, ~200 mV of steady-state region may be provided.

For reversible systems, it may be preferable to provide a scan range of from 400 to 600 mV, thus scanning from 200 to 300 mV on each side of the formal potential $E^{0\prime}$ of the redox pair. For quasi-reversible systems, it may be preferable to provide a scan range of from 600 to 1000 mV, thus scanning from 300 to 500 mV on each side of the formal potential $E^{0\prime}$ of the redox pair. The larger scan range may be preferred for quasi-reversible systems because the steady-state portion of the scan may occur where the plateau region of the scan is not as wide. In addition to redox pairs that are inherently quasi-reversible, fast scan rates may cause a redox pair that is reversible at slow scan rates to demonstrate quasi-reversible behavior. Thus, it may be preferable to provide a larger quasi-reversible scan range for a reversible redox pair at fast scan rates.

Preferably, at least 25, 50, 100, 150, or 300 mV of steady-state region is provided by the selected scan range. In another aspect, the reversing point for a cyclic or acyclic scan is selected so that from 25 to 400 mV, from 50 to 350 mV, from 100 to 300 mV, or from 175 to 225 mV of steady-state region is provided. For reversible systems, the reversing point for a cyclic or acyclic scan may be selected so that from 180 to 260 mV or from 200 to 240 mV of steady-state region is provided. For quasi-reversible systems, the reversing point for a cyclic or acyclic scan may be selected so that from 180 to 400 mV or from 200 to 260 mV of steady-state region is provided.

Figure 3E:
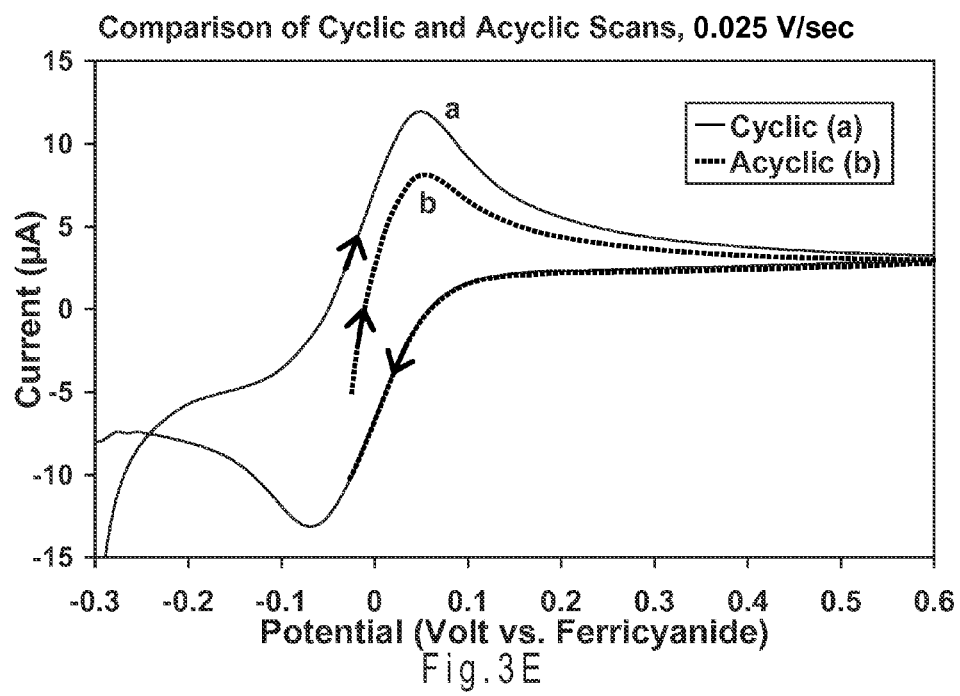
FIG. 3E compares a cyclic scan to an acyclic scan, where the forward scan of the acyclic scan was started near the formal potential $E^{o\prime}$ for the redox pair.
Figure 3F:
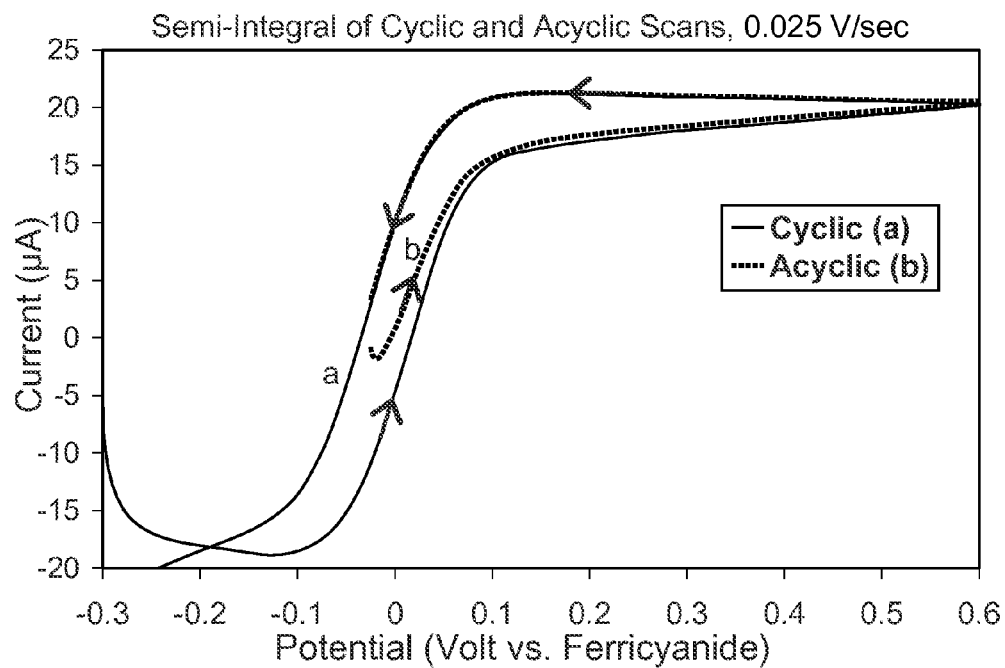
FIG. 3F compares the semi-integral currents of FIG. 3E.

Once the reversing point is selected to provide the desired steady-state region, the duration of the reverse scan may be selected for an acyclic scan. As can be seen in FIG. 3E, starting the forward scan and terminating the reverse scan at approximately −0.025 mV resulted in an acyclic scan that included more of the forward current peak than the reverse current peak. From the FIG. 3E comparison, while the peak currents obtained for the cyclic (a) and acyclic (b) scans differ, the steady-state portion of the scans were nearly the same, especially with regard to the reverse scan. When the semi-integral of the scans were plotted in FIG. 3F, the steady-state current reading of the plateau region of the return scan was further established, permitting an accurate current reading in as little as 50 mV from the reversing point.

In another aspect, the reverse scan may be terminated before the reverse current peak is reached, as depicted in FIG. 3C. When the forward scan was started at a potential sufficiently negative, such as at −0.3 mV in FIG. 3C, to the middle of the potential range of the redox pair, such as −0.05 mV in FIG. 3C, the forward scan included the full range of the redox potential of the redox pair. Thus, by terminating the reverse scan at a potential from 50 to 500 mV, from 150 to 450, or from 300 to 400 mV negative from the reversing point, for example, the reverse current peak may be excluded for the ferricyanide/ferrocyanide redox pair.

Similarly, the reverse scan also may be terminated before the reverse current peak is reached by terminating the scan when the reverse scan current deviates in value from the steady-state current. A change in the reverse scan current of at least 2%, 5%, 10%, or 25% may be used to indicate the beginning of the reverse scan current peak.

Figure 3G:
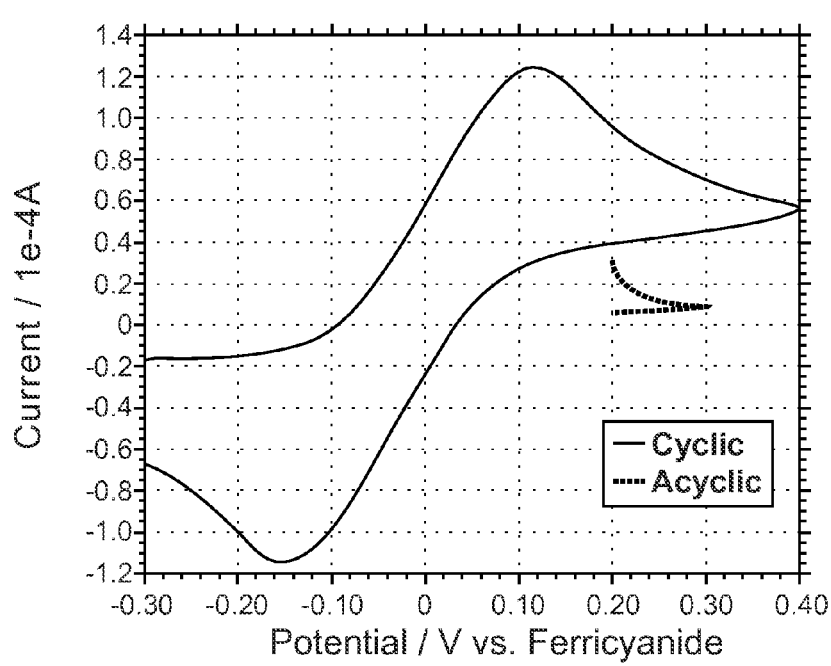
FIG. 3G shows a cyclic scan with an acyclic scan superimposed in the steady-state region.

FIG. 3G compares an acyclic scan that excludes the forward and reverse oxidation peaks of a redox pair with a fast cyclic scan. The acyclic scan rate was fast, 1 V/sec, with starting and ending points of 200 mV and a reversing point of 300 mV. Preferable scan ranges for acyclic scans within the steady-state region of a redox pair that exclude the forward and reverse oxidation peaks are from 10 to 200 mV, more preferably from 50 to 100 mV.

As seen in the graph, the current values recorded for the acyclic scan are numerically smaller than those of the cyclic scan, while the background current is lower for the acyclic scan. This beneficial background reduction was unexpectedly obtained without having to initiate the acyclic scan in the reduction peak portion of the cyclic scan. Thus, a fast and short acyclic scan within the steady-state region of a redox pair may increase the accuracy of analyte determination due to a reduction in the signal-to-background ratio.

Figure 3H:
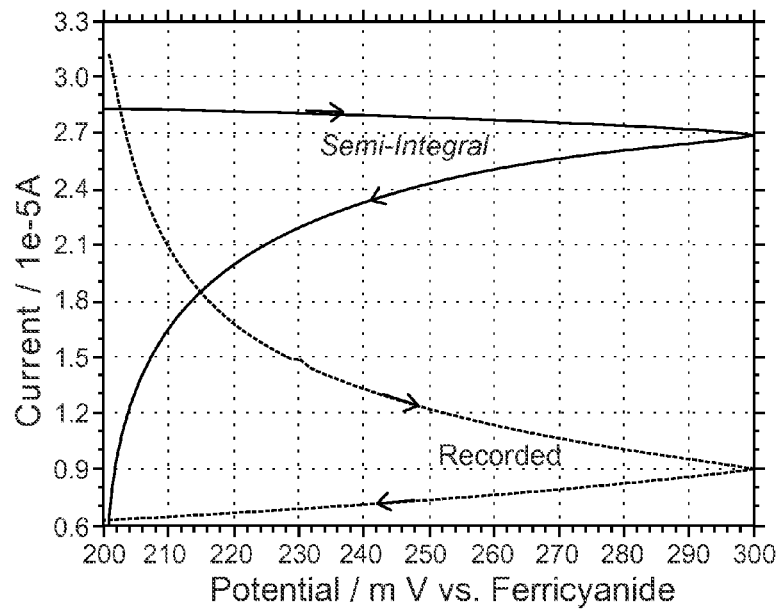
FIG. 3H compares the semi-integral and recorded current values for the acyclic scan of FIG. 3G.

FIG. 3H shows the semi-integral and recorded current values for the 200 to 300 mV acyclic scan of FIG. 3G. The decay currents of the scan are translated into a steady-state current plateau by the semi-integral data treatment. The steady-state portion of the semi-integral, for example the current value at 300 mV, may be used to determine the analyte concentration of the sample.

Cyclic and acyclic scans may provide multiple benefits in relation to linear scans. In one aspect, the portion of the reverse scan from the reversing point to the point where the reverse current peak begins may be a better representation of the steady-state region than the steady-state region of the forward scan. The steady-state region of the reverse scan may be a more accurate representation of analyte concentration for quasi-reversible redox systems or at fast scan rates because the forward scan may not show a distinct steady-state region. This phenomenon was observed in FIG. 10C, for example.

Data Treatment

Through linear, cyclic, or acyclic scanning, the concentration of the analyte in the sample may be determined. Furthermore, the hematocrit effect on the analyte concentration measurement may be determined. While the data from the scan may be treated in multiple ways to extract this and other useful information, semi-integral, derivative, and semi-derivative techniques are preferred at present.

While an overview of these data treatment methods is described below in relation to glucose analysis, a more in-depth discussion of these data treatments for electrochemical currents and the related digital implementations may be found in Bard, A. J., Faulkner, L. R., "Electrochemical Methods: Fundamentals and Applications," 1980; Oldham, K. B.; "A Signal-Independent Electroanalytical Method," *Anal. Chem.* 1972, 44, 196; Goto, M., Oldham, K. B., "Semi-integral Electroanalysis: Shapes of Neopolarograms," *Anal. Chem.* 1973, 45, 2043; Dalrymple-Alford, P., Goto, M., Oldham, K. B., "Peak Shapes in Semi-differential Electroanalysis," *Anal. Chem.* 1977, 49, 1390; Oldham, K. B., "Convolution: A General Electrochemical Procedure Implemented by a Universal Algorithm," *Anal. Chem.* 1986, 58, 2296; Pedrosa, J. M., Martin, M. T., Ruiz, J. J., Camacho, L., "Application of the Cyclic Semi-Integral Voltammetry and Cyclic Semi-Differential Voltammetry to the Determination of the Reduction Mechanism of a Ni-Porphyrin," *J. Electroanal. Chem.* 2002, 523, 160; Klicka, R, "Adsorption in Semi-Differential Voltammetry," *J. Electroanal. Chem.* 1998, 455, 253.

Semi-Integration

Semi-integration of a voltammogram may separate the diffusion-limited steady-state current from the hematocrit affected equilibrium current (initial peak). The semi-integral of the experimentally obtained voltammetric current i(t) has the following mathematical form:

$$\frac{d^{-1/2}}{dt^{-1/2}} i(t) = I(t) = \frac{1}{\pi^{1/2}} \int_0^\tau \frac{i(u)}{(t-u)^{1/2}} du \tag{2}$$

where i(t) is the time function of the voltammetric current obtained during the scan; I(t) is a transformation and the semi-integral of i(t); u is a transformation parameter; and $d^{-1/2}/dt^{-1/2}$ is the semi-integration operator.

At a sufficiently high oxidation potential, the steady-state semi-integral current is given by:

$$I_{lim} = nFAD^{1/2}C \; (\text{coul/sec}^{1/2}) \tag{3}$$

where $I_{lim}$ is the diffusion-limited steady-state current under the condition of the surface concentration of the oxidizable species being zero. Note that the unit of semi-integral current is coul/sec$^{1/2}$, which is not the traditional unit for expressing electrical current, which is coul/sec.

For simplicity, $I_{lim}$ is referred to as the steady-state semi-integration current (SI) with a unit of coul/sec$^{1/2}$. The SI current (coul/sec$^{1/2}$) is only a half-step integration from current (coul/sec). The half-step integration is fundamentally different from coulometry because in coulometry a full integral is applied to the i-t curve to provide the total charge passing through the electrodes.

Although equation (2) gives a theoretical definition of the semi-integral, for digital processing the i-t data may be divided into N equally spaced time intervals between t=0 and t=NΔt. One such digital processing algorithm is given by equation (4) where t=kΔt and u=jΔt, and i is determined at the midpoint of each interval.

$$I(k\Delta t) = \frac{1}{\pi^{1/2}} \sum_{j=1}^{j=k} \frac{i(j\Delta t - 1/2\Delta t)\Delta t^{1/2}}{\sqrt{k-j+1/2}} \tag{4}$$

A preferred algorithm for digital processing is given by:

$$I(k\Delta t) = \frac{1}{\pi^{1/2}} \sum_{j=1}^{j=k} \frac{\Gamma(k-j+1/2)}{(k-j)!} \Delta t^{1/2} i(j\Delta t) \quad (5)$$

where $\Gamma(x)$ is the gamma function of x, where $\Gamma(1/2)=\pi^{1/2}$, $\Gamma(3/2)=1/2\pi^{1/2}$, $\Gamma(5/2)=3/2*1/2\pi^{1/2}$, etc.

From equation (3) it may be seen that the steady-state semi-integral current lacks the time-dependence factor of conventional amperometric methods. Thus, the semi-integral current response may be considered a series of plateau currents, instead of the continuously changing amperometric currents obtained from conventional amperometry. Because the semi-integration allows for quantification of the steady-state current, a faster scan rate may be used than when peak currents are quantified. Thus, linear, cyclic, or acyclic voltammetry in combination with semi-integration may rapidly generate steady-state currents in response to glucose concentrations. In this manner, the disadvantages of the long wait times of coulometry and the non-steady-state nature of the current in amperometry may be reduced.

Equation (3) also shows that reversible or quasi-reversible redox pairs are preferred for use with semi-integration. This is because the semi-integral from a reversible or quasi-reversible redox pair can exhibit a sharp transition from the reduced state to the oxidized state (and vice versa) and a wide steady-state region, thus making the transition easier to determine. Ferricyanide/ferrocyanide and the +3 and +2 states of ruthenium hexaamine are examples of redox pairs demonstrating preferred reversible (slow scan) or quasi-reversible (fast scan) behaviors.

Poorly activated electrodes may not provide an acceptable steady-state condition even with reversible or quasi-reversible redox pairs. Thus, electrode activation procedures, such as those described in U.S. Pat. No. 5,429,735, may be used to achieve the preferred electrode activity.

Semi-Derivative

In addition to semi-integrals, semi-derivatives of a voltammogram also may be used to quantify the analyte by measuring the peak of the semi-derivative. The semi-derivative of the experimentally obtained voltammetric current i(t) has the following mathematical forms:

$$\frac{d^{1/2}}{dt^{1/2}} i(t) \quad (6)$$

$$\frac{d^{1/2}}{dt^{1/2}} i(t) = \frac{dI(t)}{dt} = \frac{d}{dt}\left[\frac{1}{\pi^{1/2}} \int_0^t \frac{i(u)}{(t-u)^{1/2}} du\right], (coul/\sec^{3/2}) \quad (7)$$

where I(t) is the semi-integral of the time function i(t).

Figure 4A:
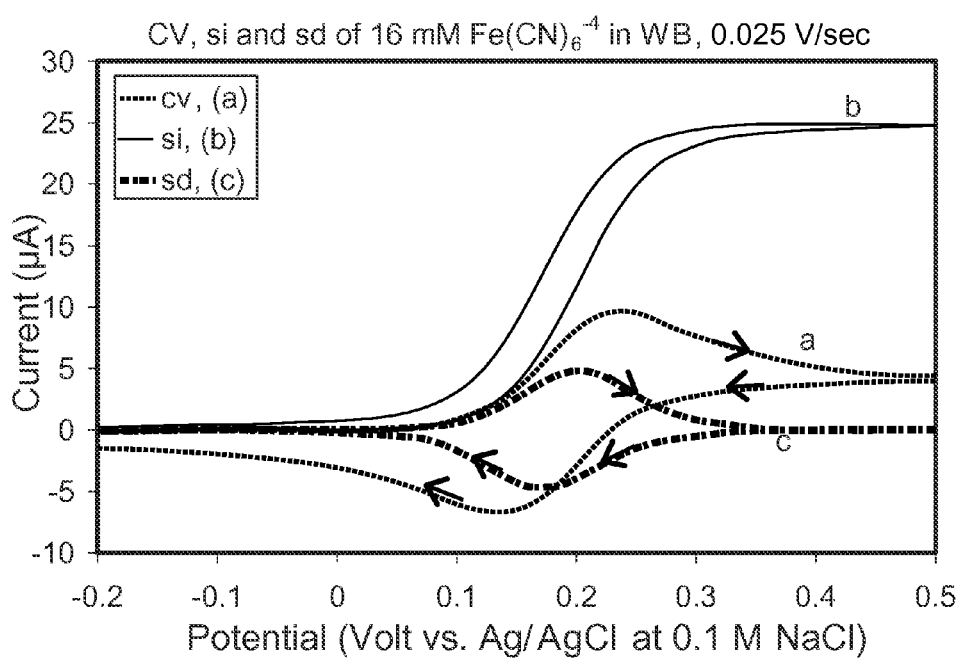
FIG. 4A depicts the cyclic voltammogram, semi-integral, and semi-derivative of 16 mM ferrocyanide in a 20% hematocrit whole blood sample.
Figure 4B:
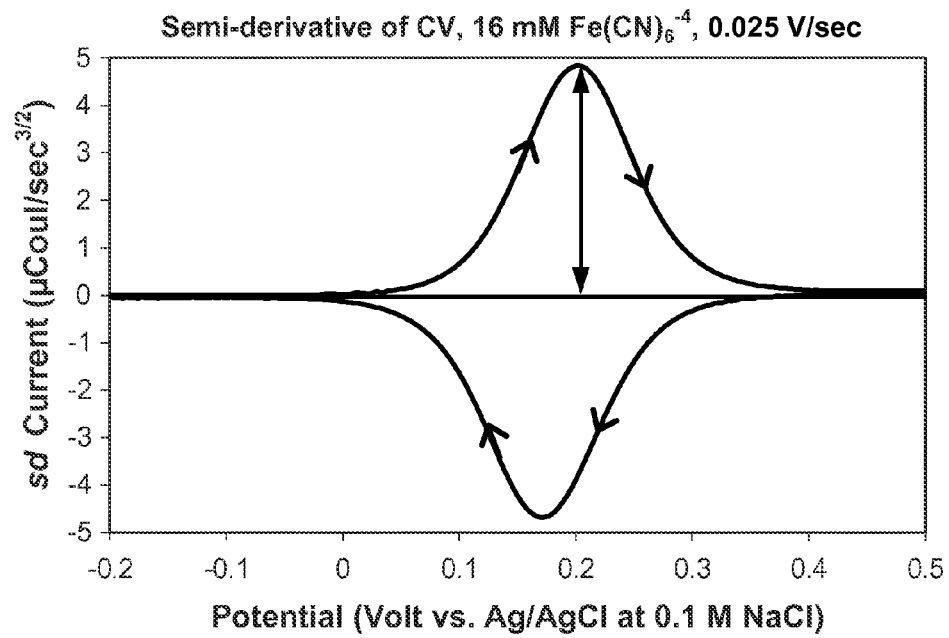
FIG. 4B is an enlargement of the semi-derivative curve of FIG. 4A.

One implementation of a semi-derivative is to take a full step derivative of the semi-integral, as shown above in equation (7). Unlike the peak and steady-state plateau regions representing the voltammetric scan in semi-integral plots, semi-derivative plots convert the voltammetric scan data into a peak centered at the transition of the redox pair. FIG. 4A depicts the cyclic voltammogram, semi-integral, and semi-derivative of 16 mM ferrocyanide in a 20% hematocrit whole blood sample. In this instance, the working electrode of the sensor strip lacked enzyme and oxidized mediator. FIG. 4B is an enlargement of the semi-derivative curve of FIG. 4A showing the peak height for the forward scan. The value of the forward or reverse scan peak height may be correlated with the analyte concentration of the sample.

Hematocrit Effect

The normal hematocrit range (RBC concentration) for humans is from 20% to 60% and is centered around 40%. The hematocrit effect refers to the difference (bias) between a reference glucose concentration reading value obtained from a reference instrument, such as the YSI 2300 STAT PLUS™ available from YSI Inc., Yellow Springs, Ohio, and an experimental glucose concentration reading obtained from the methods described above. The difference between the reference and experimental readings results from the varying hematocrit levels between specific whole blood samples.

While the glucose concentration in whole blood samples is the same for different hematocrit levels, in diffusion based analytic methods, such as amperometry, the higher the hematocrit, the lower the measured amperometric current. For whole blood hematocrit levels of 20, 40, and 60%, the obtained current readings will be different in the order of 20%>40%>60% for the same glucose concentration. This difference between the 20% and 60% current readings constitutes the hematocrit bias span for glucose readings obtained for the whole blood sample. The inaccuracy in a glucose determination introduced by varying hematocrit levels for each whole blood sample may constitute a major source of error in the analysis.

For example, if the experimentally obtained glucose reading is made with reference to the current reading obtained for glucose in plasma and the calibration method presumes a 40% hematocrit content in the sample, then the higher current readings obtained from whole blood samples containing 20% hematocrit will translate into a positive bias with regard to the 40% calibration line. Similarly, the lower current readings obtained from whole blood samples containing 60% hematocrit will translate into a negative bias with regard to the 40% calibration line.

Hematocrit Reduction

Figure 10A:
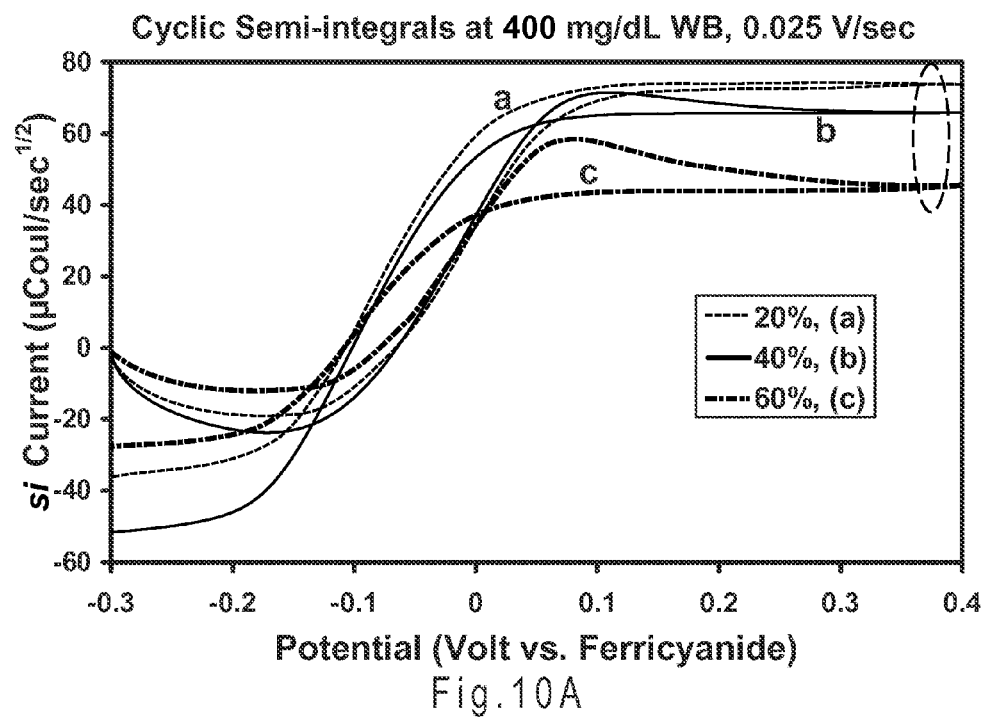
FIGS. 10A-10C show the semi-integral currents corresponding to the cyclic scans of FIGS. 9A-9C.

In one aspect, a slow scan rate may be combined with linear, cyclic, or acyclic scanning and semi-integration to reduce the hematocrit bias of the concentration determination when whole blood is analyzed for glucose concentration. FIG. 10A shows that for a slow 25 mV/sec scan rate a large peak is observed in the forward scan portion of the semi-integral for 60% hematocrit (line c), while a smaller peak is observed for 40% hematocrit (line b). The 20% hematocrit line (a) lacks a significant peak. Thus, the peak portion of the semi-integral plot is responsive to the hematocrit content of the sample and the magnitude of the peak may be quantitatively related to the hematocrit level.

Figure 15A:
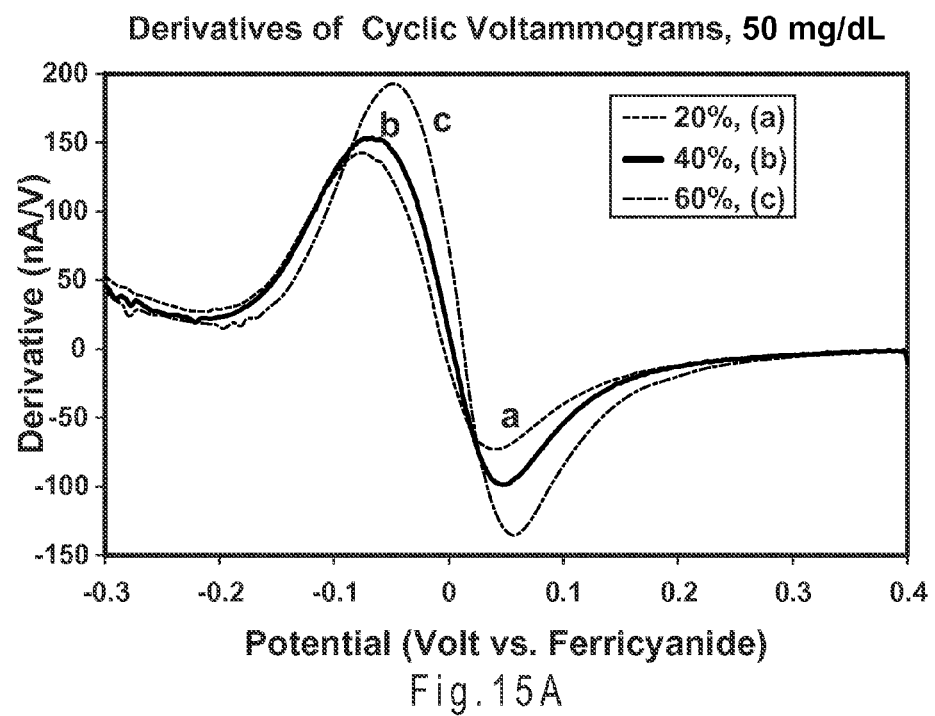
FIGS. 15A-15C show the derivative currents of the forward scans from FIGS. 7A-7C plotted versus voltage.
Figure 15B:
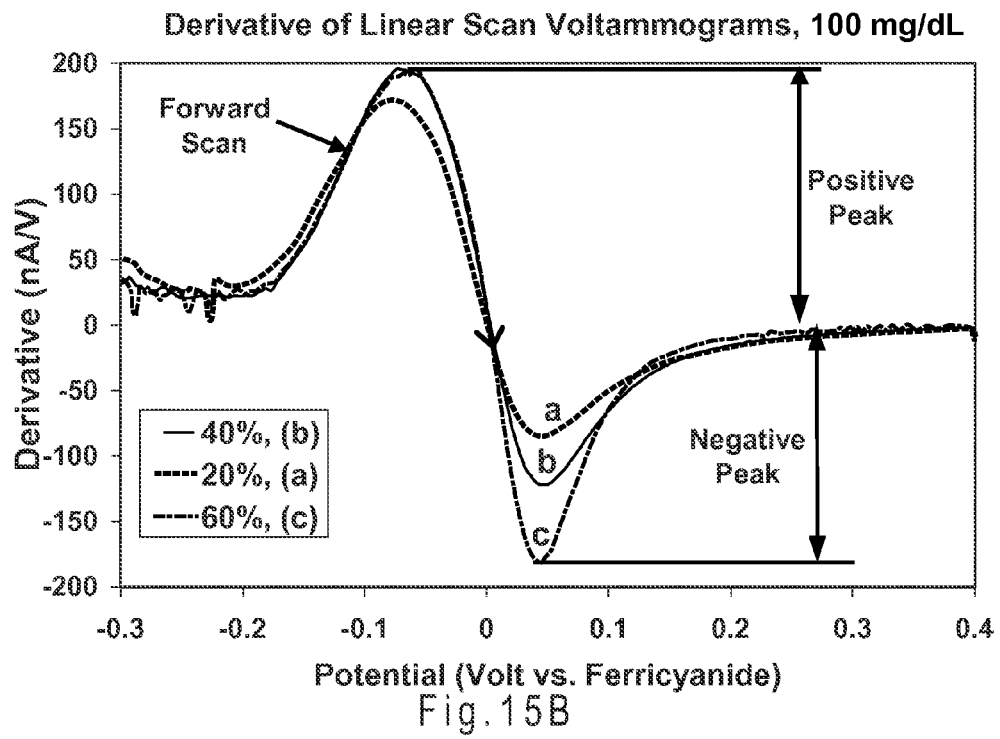
Figure 15C:
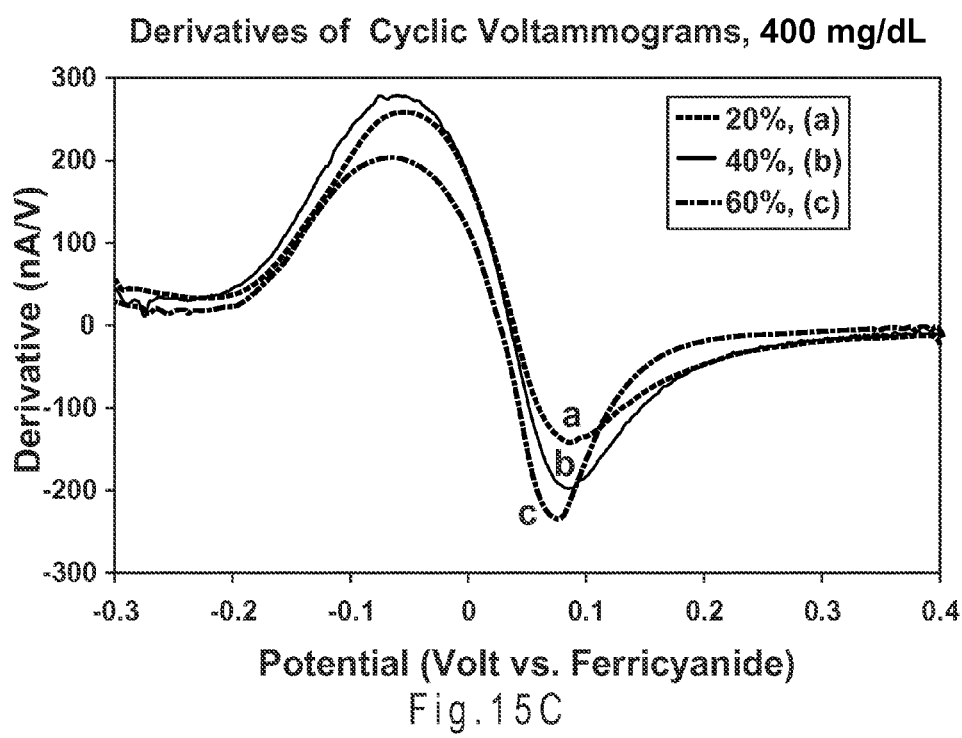

In another aspect, linear, cyclic, or acyclic scans may be combined with derivative data treatment to reduce the hematocrit bias of the concentration determination when whole blood is analyzed for glucose concentration. FIGS. 15A-15C depict the derivatives of the cyclic voltammograms of FIGS. 7A-7C. These derivative plots show an initial increase in current as voltage increases, followed by a decrease, and finally a steady-state region. The hematocrit effect may be seen in the negative peak located at about 0.1 volts in FIGS. 15A-15C, with higher RBC concentrations reflected as more negative peak values.

While the values of the positive and negative derivative peaks, such as those depicted in the derivative plot of FIG. 15B, are concentration-dependent, the ratio of the negative peak to the positive peak cancels out the concentration dependence, thus being hematocrit-dependent. Because this ratio (HI-DER) is concentration independent and hematocrit dependent, the ratio indicates the percent hematocrit in the sample. Thus, this ratio of the derivative peaks may be used to determine a hematocrit compensation equation for analyte determination, as described further below.

Figure 4C:
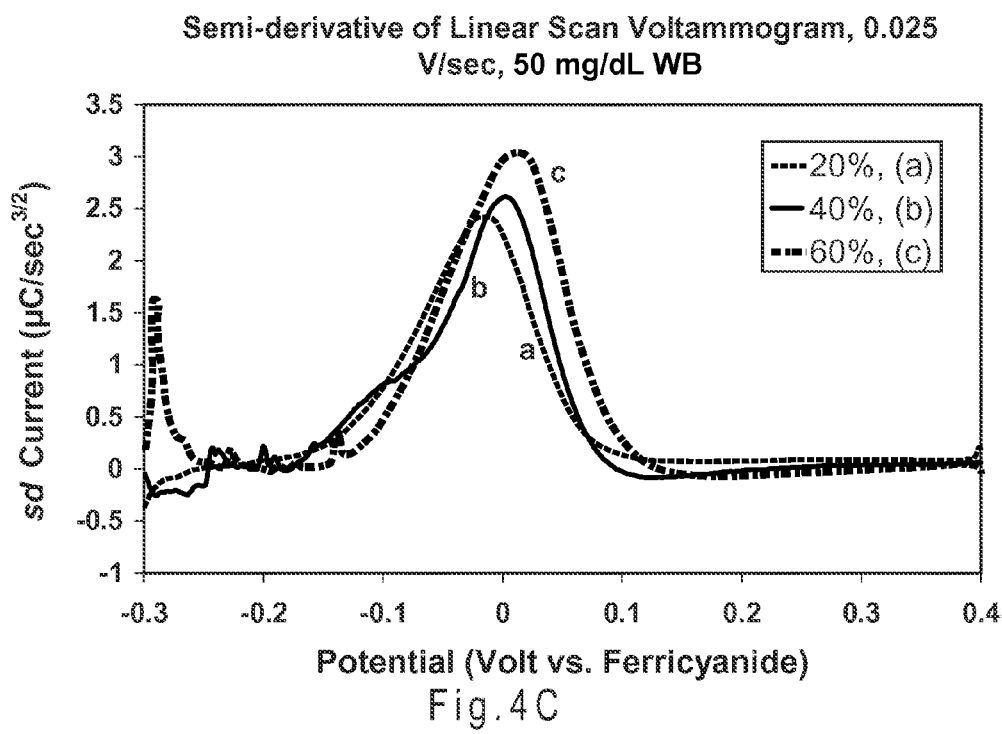
FIGS. 4C-4E depict the semi-derivative curves from the forward linear scan portions of the cyclic voltammograms of FIGS. 7A, 7B and 7C, below.
Figure 4D:
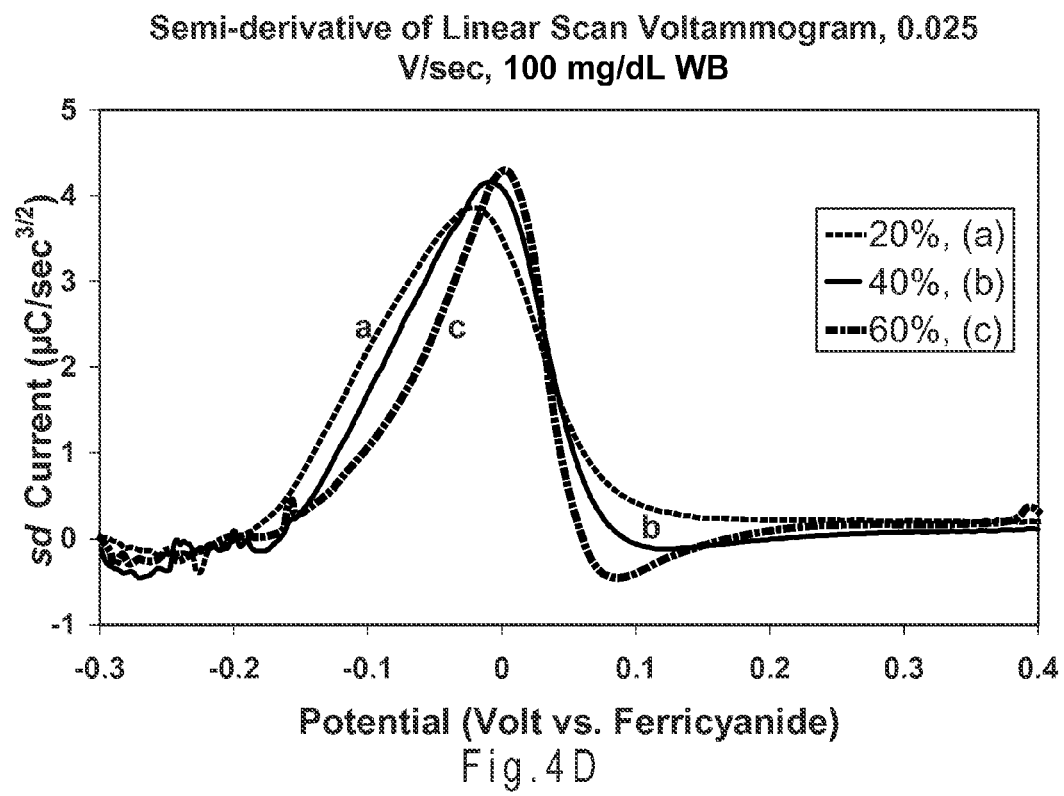
Figure 4E:
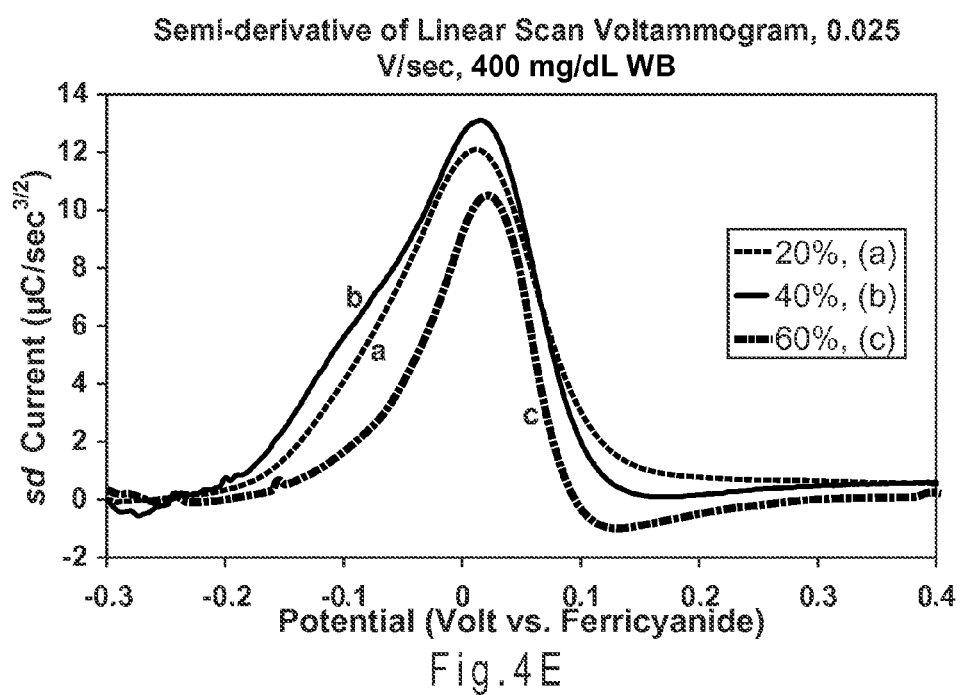

In another aspect, linear, cyclic, or acyclic scans may be combined with semi-derivative data treatment to reduce the hematocrit bias of the concentration determination when whole blood is analyzed for glucose concentration. FIGS. 4C, 4D, and 4E depict the semi-derivative curves from the forward linear scan portions of the cyclic voltammograms of FIGS. 7A, 7B and 7C at 50, 100, and 40 mg/dL glucose after subtraction of the background voltammogram (0 mg/dL glucose).

Figure 4F:
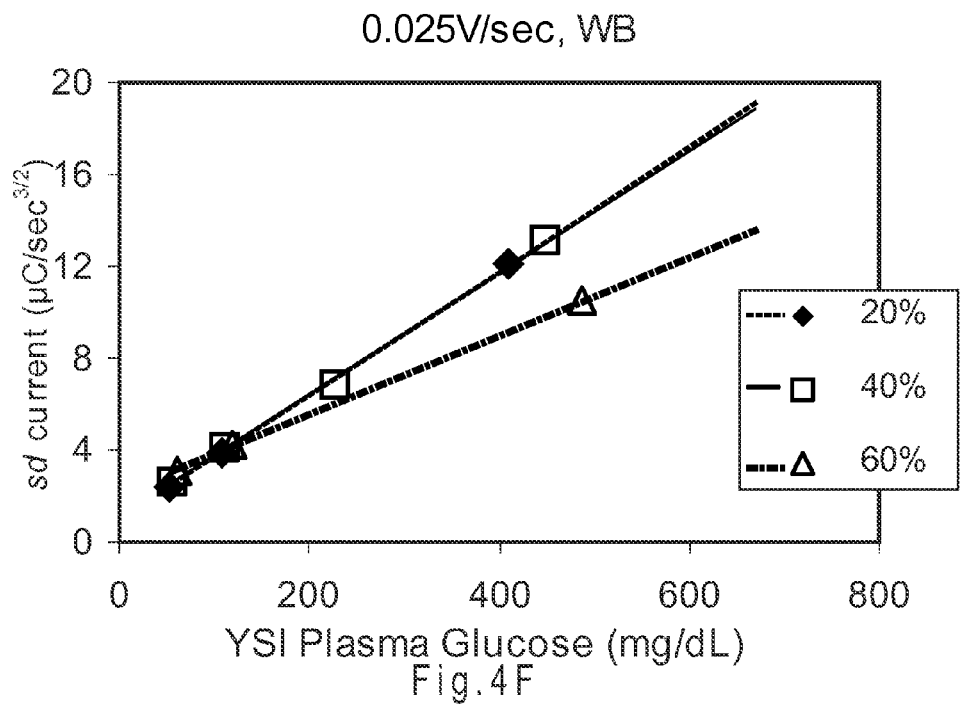
FIG. 4F depicts the semi-derivative currents from FIGS. 4C-4E.

FIG. 4F depicts the semi-derivative currents from FIGS. 4C, 4D, and 4E plotted against the reference glucose concentrations at each hematocrit level. The overlap of the 20% and 40% hematocrit lines establishes that the hematocrit effect was substantially eliminated at the lower 20% value. The hematocrit bias between the 40% hematocrit line and the 60% hematocrit line also was reduced in relation to that obtained from the steady-state portion of the unaltered data from the voltammogram or from the semi-integration of the voltammogram. Thus, the semi-derivative data treatment may inherently provide hematocrit compensation for glucose determination.

Figure 4G:
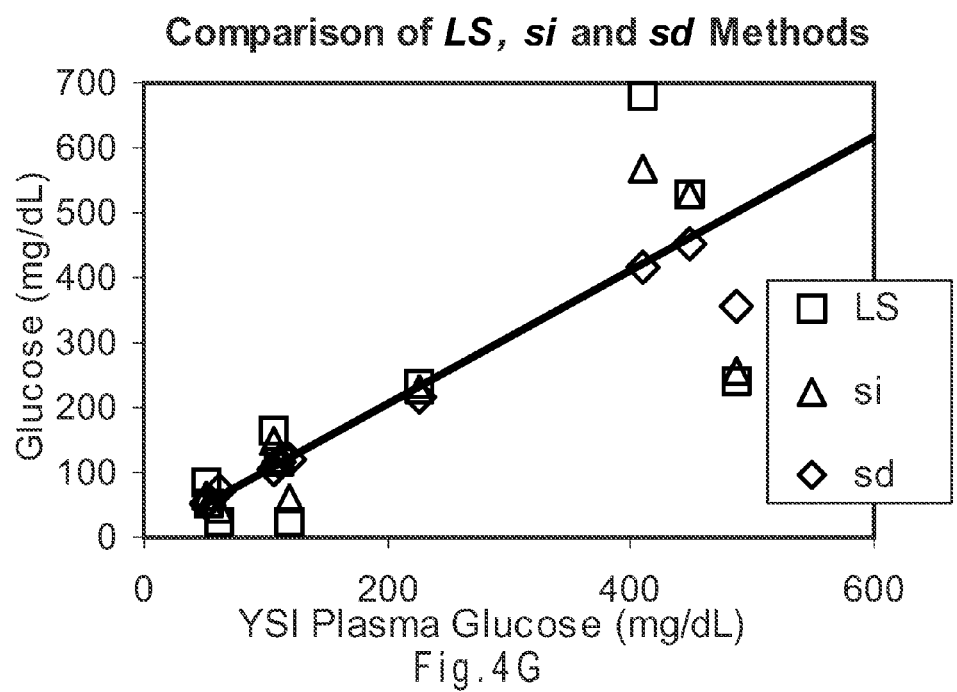
FIG. 4G depicts a comparison of the calculated glucose values from the unaltered forward scan of the voltammogram (LS), the semi-integral of the voltammogram data (si), and the semi-derivative of the voltammogram data (sd).

FIG. 4G depicts a comparison of the data from the unaltered forward scan of the voltammogram (LS), the semi-integral of the voltammogram data (si), and the semi-derivative of the voltammogram data (sd). The glucose values were calculated using the calibration curve at the 40% hematocrit level. As may be seen from the plot, the semi-derivative data corresponds well to the line obtained from the YSI reference instrument.

Semi-integration and derivative data treatments allow for identification and quantification of the portion of the current scan affected by the hematocrit effect. Thus, these data treatments allow for a reduction of the hematocrit bias that would otherwise affect the determination of the analyte concentration. Semi-derivative data treatment may allow for a reduction of the hematocrit bias that would otherwise affect the determination of the analyte concentration without a compensation equation, as discussed further below.

Figure 10B:
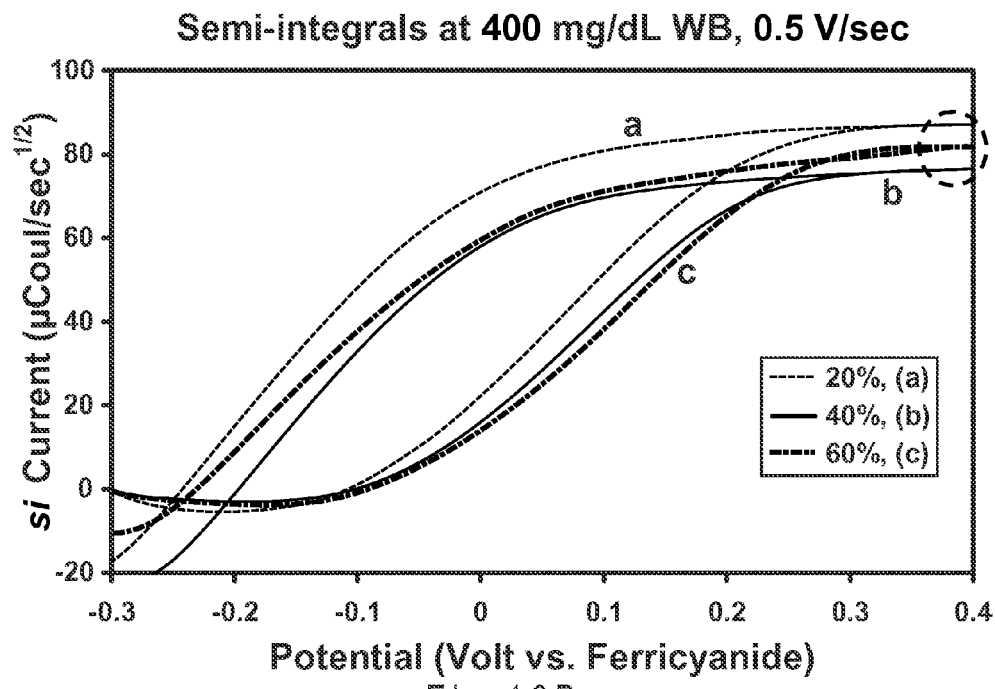
Figure 10C:
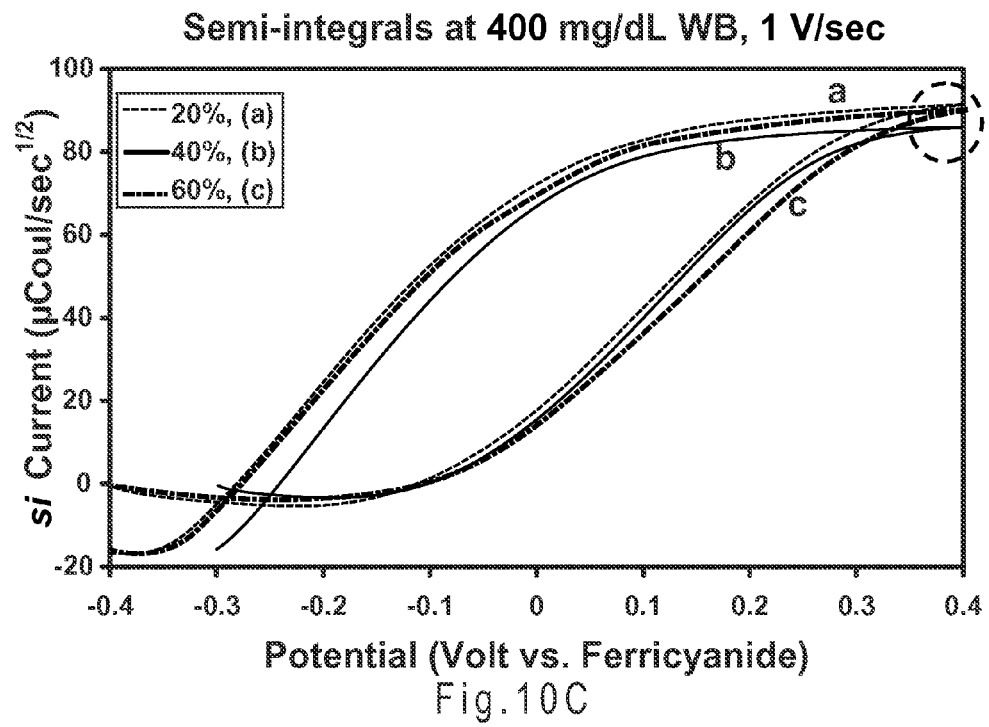

In another aspect, faster scan rates, such as the 500 and 1000 mV/sec scan rates of FIGS. 10B and 10C, may be combined with linear, cyclic, or acyclic scanning and semi-integration, derivative, or semi-derivative data treatment to reduce the hematocrit bias and measure the glucose content of whole blood. Faster scan rates also may provide the benefit of shorter scan times, a significant benefit for the user.

When the total length of the scan is relatively long as in conventional amperometry or slow scan voltammetry, the diffusion of the mediator and the current measured will be largely affected by the RBC content of the sample. Conversely, if the scan rate is fast, such as 500 mV/sec, the time required to reach a 400 mV termination point from a −200 mV starting point is 1.2 seconds. Similarly, the 400 mV termination point may be reached after 0.6 seconds at a 1000 mV/sec scan rate or after 0.3 seconds at a 2000 mV/sec scan rate. Thus, total scan times of at most 3 seconds, 1.5 seconds, 1 second, or 0.5 second may reduce the hematocrit bias on the concentration measurement without mathematical removal.

Determining Analyte Concentration

Figure 5:
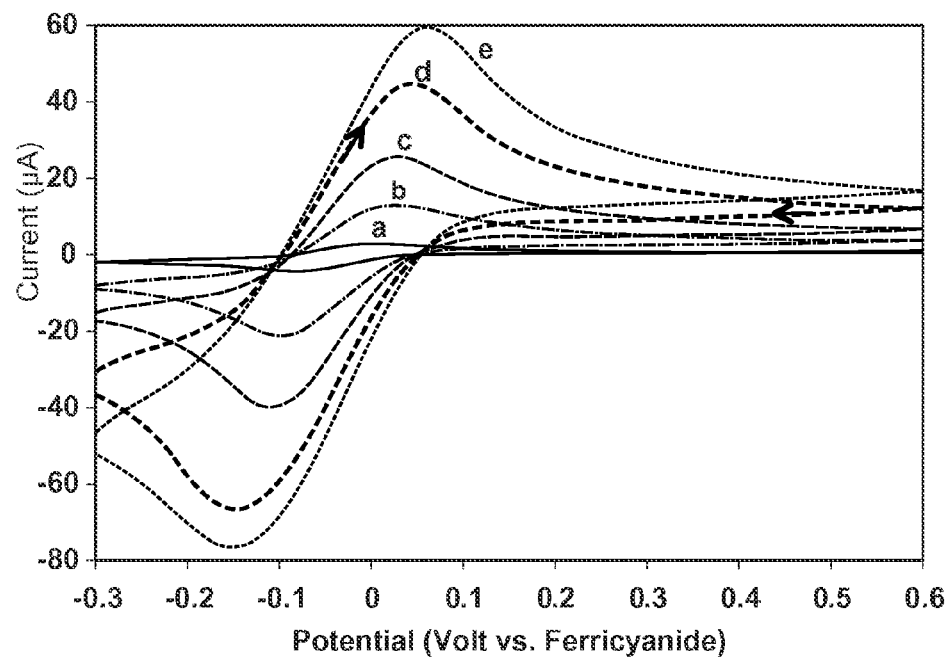
FIG. 5 is a set of cyclic voltammograms showing the effect of varying glucose concentrations in aqueous solutions.
Figure 6:
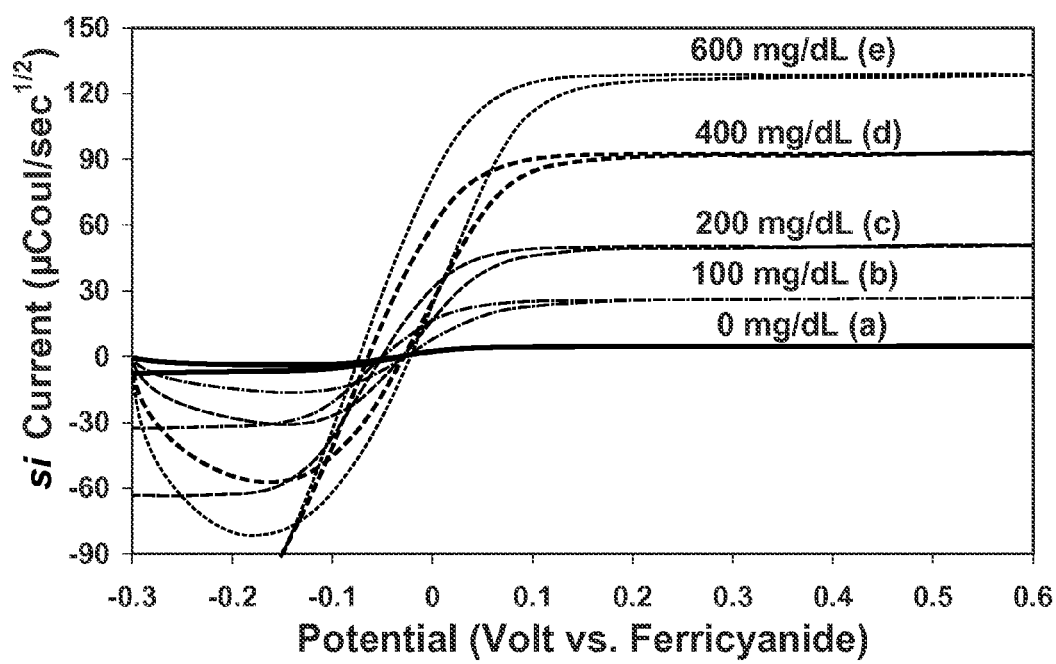
FIG. 6 shows the semi-integral currents of the voltammograms of FIG. 5.

FIG. 5 depicts the effect on the cyclic voltammograms when the glucose concentration of an aqueous solution is increased. Lines representing glucose concentrations of 0 mg/dL (line a), 100 mg/dL (line b), 200 mg/dL (line c), 400 mg/dL (line d), and 600 mg/dL (line e) are shown. The scanning rate was 25 mV/sec. FIG. 6 presents the scan data from FIG. 5 after conversion to semi-integral currents by a semi-integral data treatment. Thus, difference in each glucose concentration is apparent from the X-axis of FIG. 6.

The shape of a cyclic voltammogram will change as the whole blood sample is scanned. The cyclic voltammogram will show a displacement of the voltammetric currents that varies with the hematocrit and the glucose concentration, especially the currents near the steady-state portion (0.3-0.4V in FIGS. 7A-7C). The change may be seen in FIGS. 7A-7C where the voltammograms are shown for glucose concentrations of 50 mg/dL (7A), 100 mg/dL (7B), and 400 mg/dL (7C) respectively, and also for 20, 40, and 60% hematocrit (curves a, b, c respectively) for each of the glucose concentrations. The scanning rate was 25 mV/sec. As expected in view of the hematocrit effect, the higher the hematocrit percentage in the sample, the greater the reading for the same glucose concentration. The corresponding semi-integral plots of the cyclic scans are shown as FIGS. 8A-8C, where the displacement between the steady-state currents are highlighted with a circle. FIGS. 7D-7F and 8D-8F present the scan data and the corresponding semi-integrals for an analogous acyclic scan.

Scanning may be performed over the range of −600 mV to +600 mV; however, the preferred scan range depends on the redox pair (mediator) used in the biosensor. Generally, the measuring device will be programmed during the manufacturing stage with the range which is to be scanned.

Figure 9A:
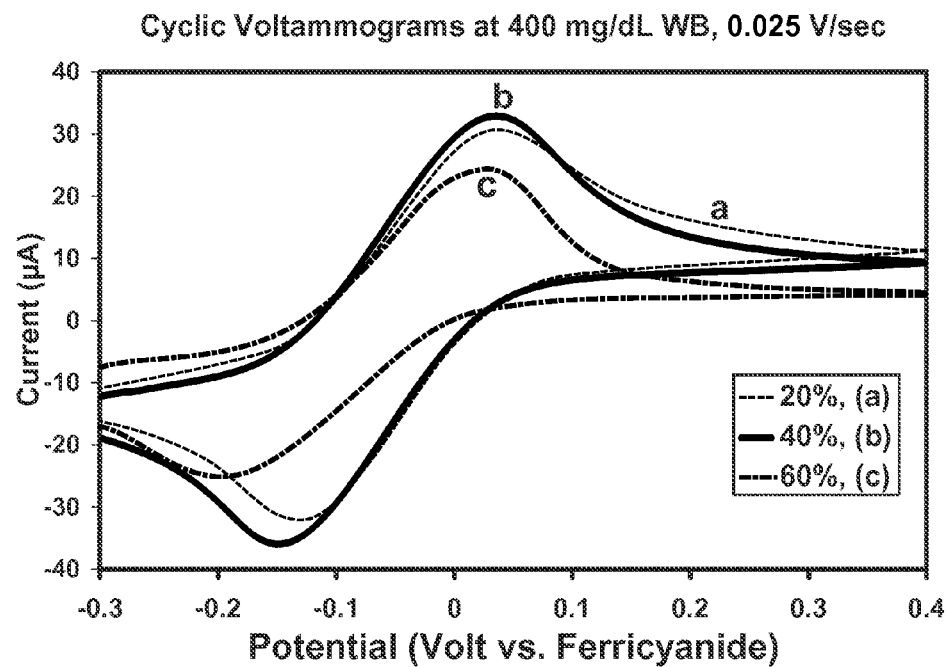
FIGS. 9A-9C are cyclic voltammograms illustrating the effect of varying scanning rate on the hematocrit effect.
Figure 9B:
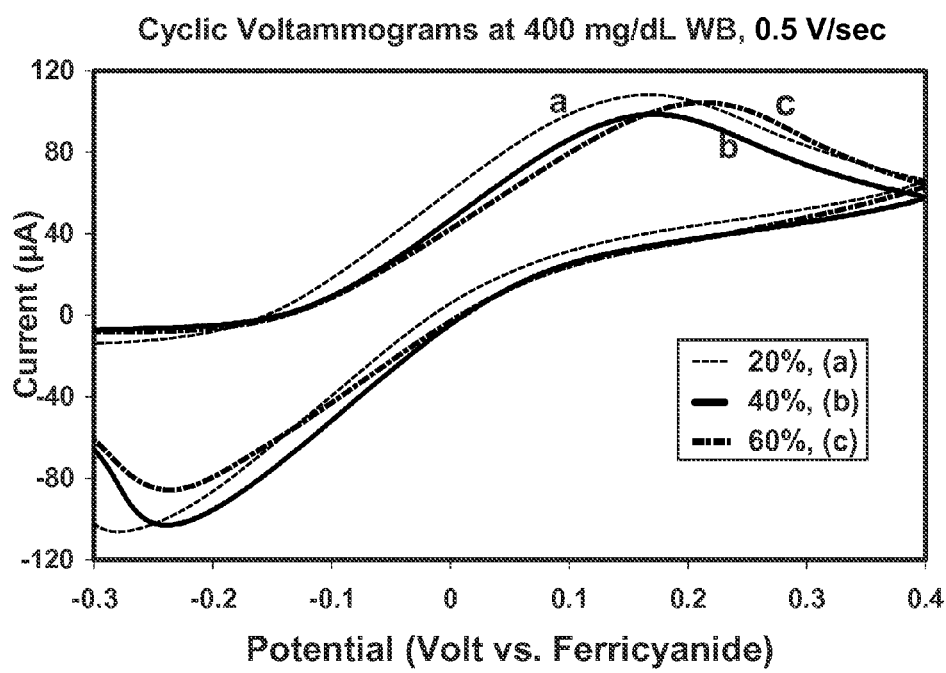
Figure 9C:
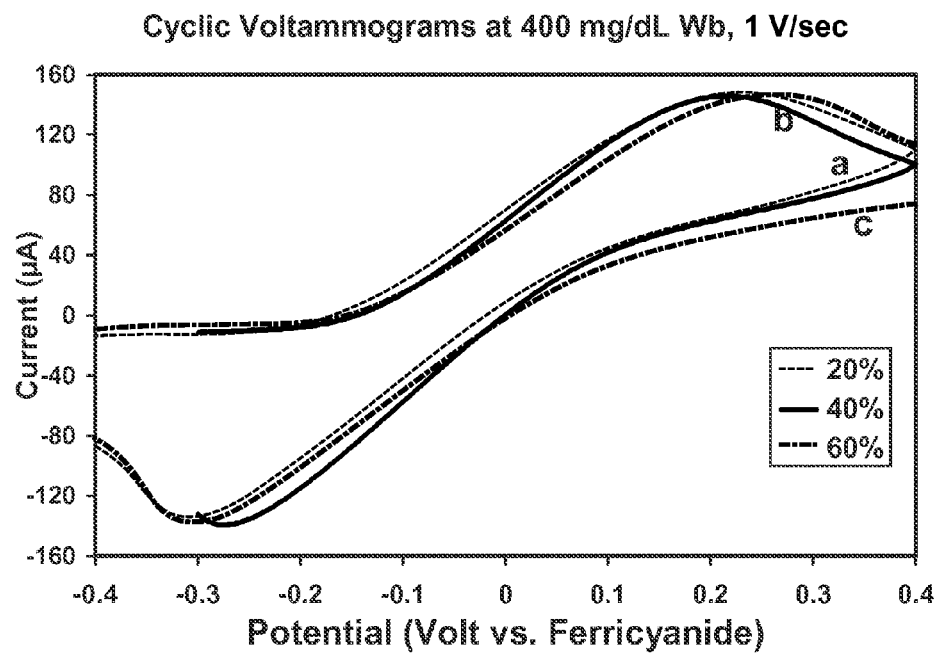

FIGS. 9A-9C depict the results for scanning rates of 25 mV/sec, 500 mV/sec, and 1000 mV/sec, respectively, for blood samples containing 400 mg/dL of glucose. As the scan rate increases from 25 mV/sec in FIG. 9A to 500 mV/sec in FIGS. 9B and 1000 mV/sec in FIG. 9C, the initial hematocrit affected peak decreases. Furthermore, peak current values are related to the hematocrit values of the sample (a is 20%, b is 40%, c is 60% hematocrit), with greater hematocrit percent generally correlating with faster decay from peak currents at slow scan rates.

The semi-integral plots corresponding to the voltammograms of FIGS. 9A-9C are shown as FIGS. 10A-10C, respectively. As seen from the circled reversing points in the 25 mV/sec FIG. 10A scan, the steady-state currents of the 20%, 40% and 60% hematocrit lines were separated with regard to the Y-axis. As the scan rates were increased to 500 mV/sec in FIG. 10B and to 1000 mV/sec in FIG. 10C, the Y-axis separation of the 20%, 40%, and 60% hematocrit lines decreased. Thus, as the scan rate increases, the hematocrit affected portion of the scan is diminished.

Figure 11A:
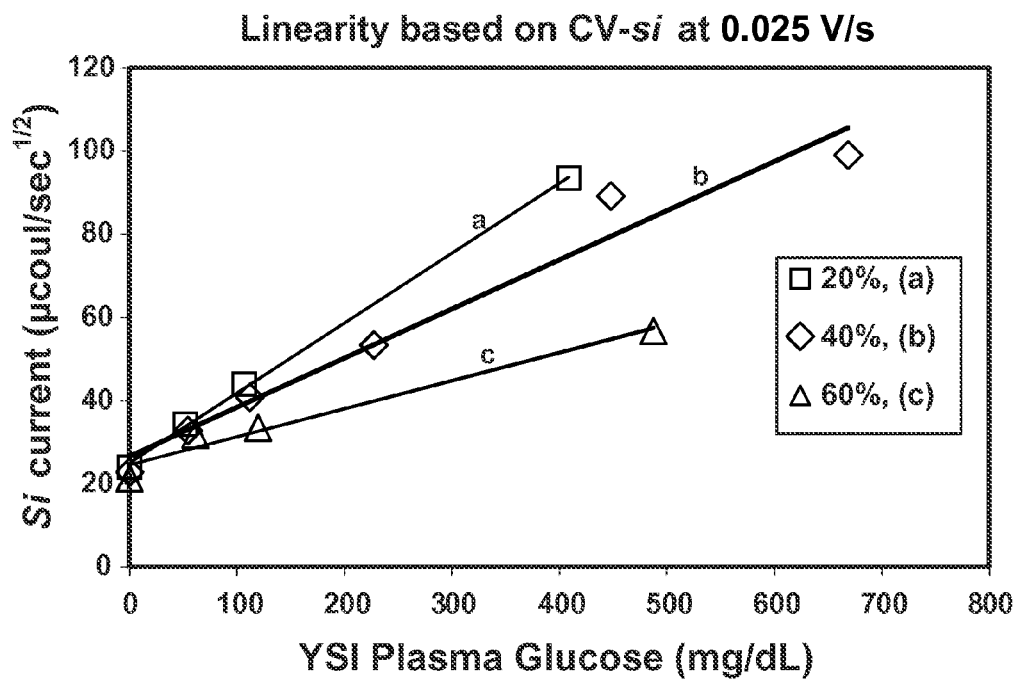
FIGS. 11A-11C show the correlation between the semi-integral lines of FIGS. 10A-10C based on the experimental results of FIGS. 9A-9C and the reference glucose concentration of each sample
Figure 11B:
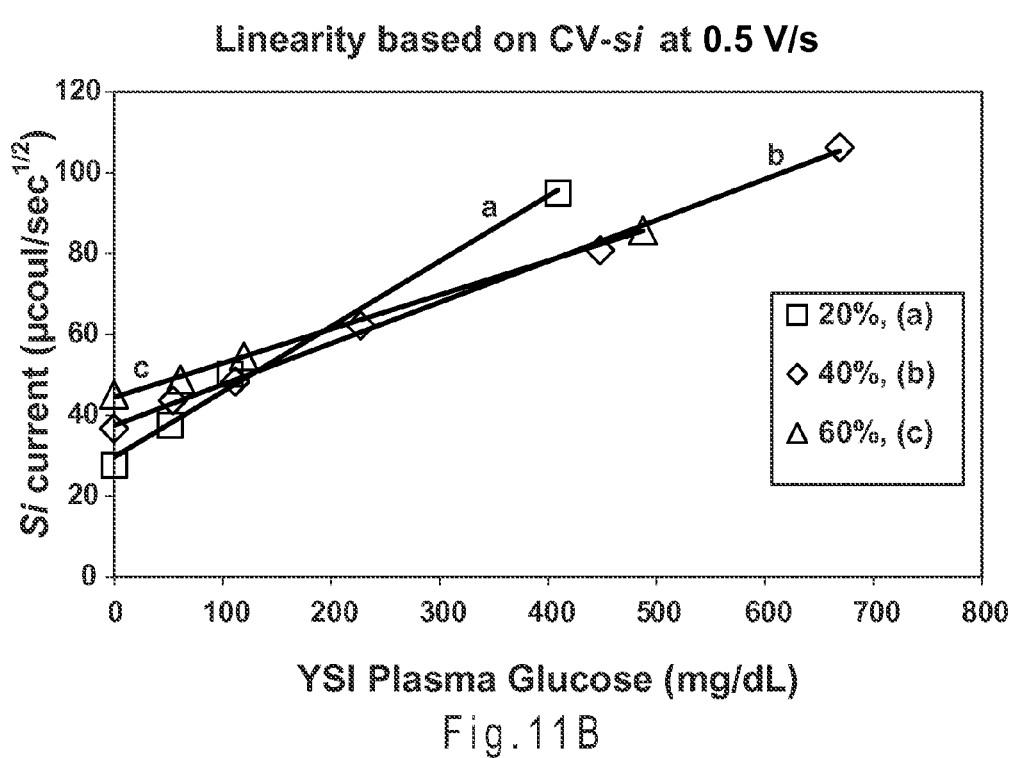
Figure 11C:
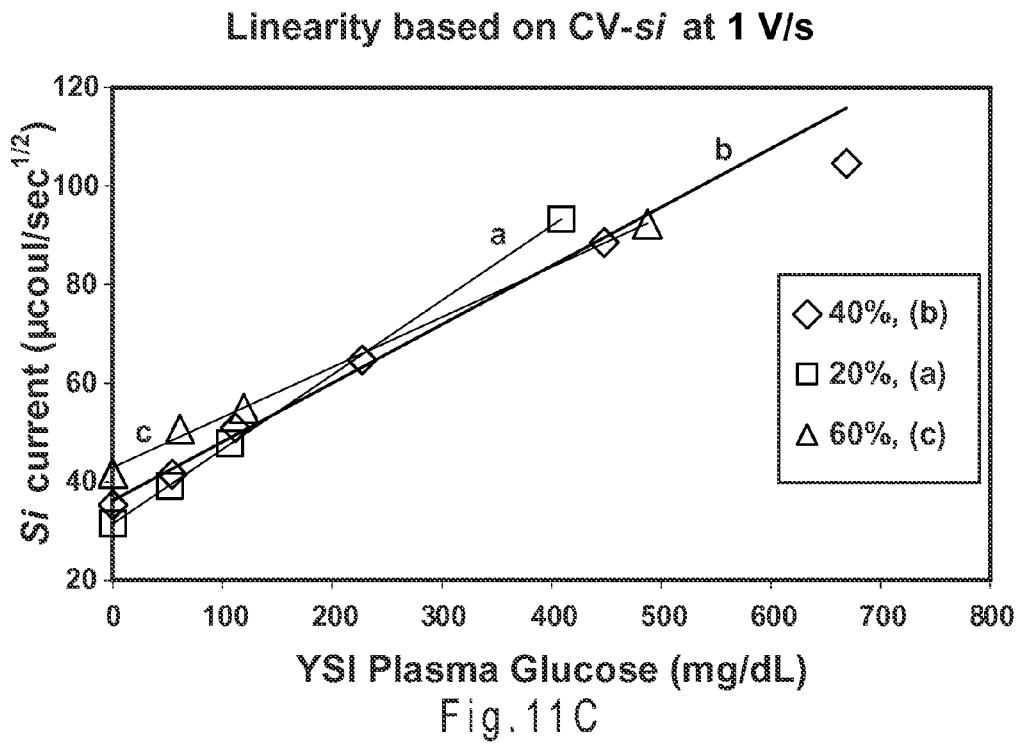

FIGS. 11A-11C show the correlation between the semi-integral lines of FIGS. 10A-10C based on the experimental results of FIGS. 9A-9C and the reference glucose concentration of each sample. The reference glucose concentration values from the YSI instrument (X-axis) were compared to the semi-integral currents (Y-axis) for each hematocrit percentage. As expected, the 25 mV/sec scan of FIG. 11A shows the largest bias attributable to the hematocrit effect, while the faster 500 and 1000 mV/sec scans of FIGS. 11B and 11C, respectively, show less bias.

Figure 12:
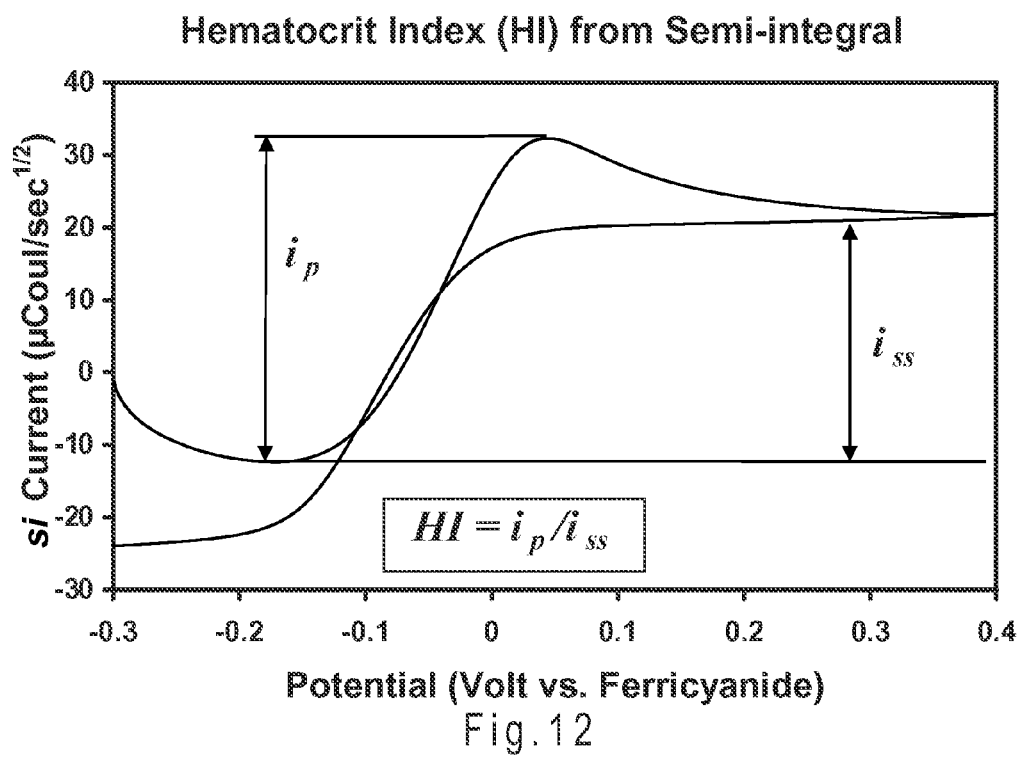
FIG. 12 shows a semi-integral current peak and a semi-integral current steady-state value, which may be used to determine a Hematocrit Index.

The ratio of the peak to steady-state current values in a semi-integral plot may be referred to as the Hematocrit Index (HI), which may be defined as the semi-integral current peak ($i_p$) divided by the semi-integral current steady-state value ($i_{ss}$), as shown in FIG. 12. The calculated Hematocrit Index (HI) was correlated with the actual %-hematocrit content of the sample to provide the correlation line shown in FIG. 13A. As previously discussed with regard to a derivative data treatment, a HI-DER ratio also may be used to provide the correlation line.

Figure 13A:
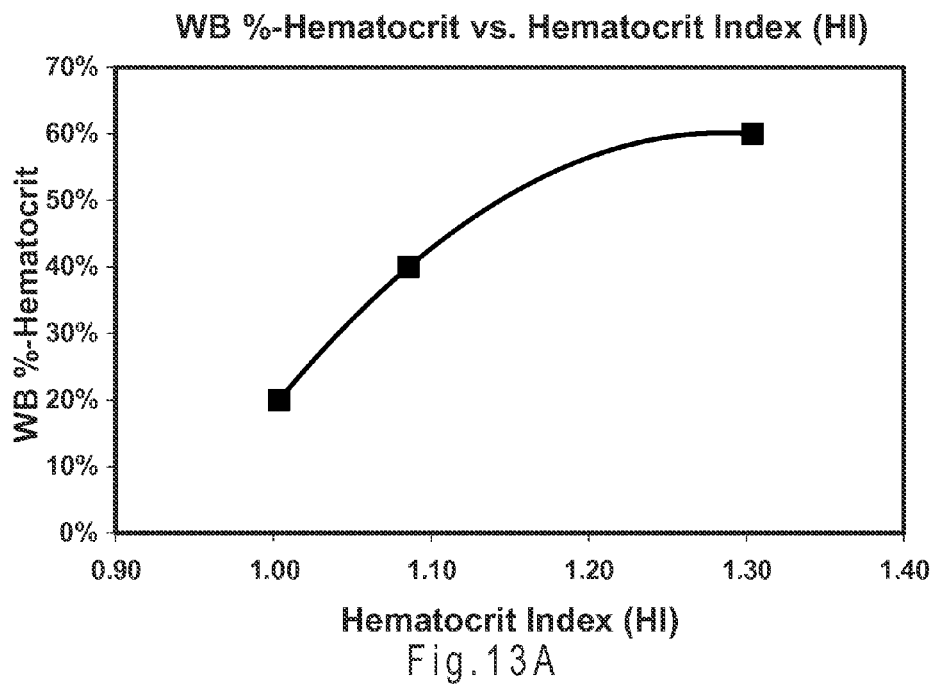
FIG. 13A shows the correlation of the Hematocrit Index with the hematocrit content of whole blood.

A compensation equation that describes the slope or the intercept and the slope of a correlation line, such as that shown in FIG. 13A for a semi-integral data treatment, may then be determined. Once the compensation equation is determined, the glucose concentration of the sample, compensated for the hematocrit effect, may be determined by plugging a desired current value, such as the steady-state current value, into the equation. Thus, the ratio of the peak to steady-state current value for semi-integral data treatment, or the ratio of the negative peak to the positive peak for derivative data treatment, may be used to correct for the analytical bias attributable to the hematocrit effect.

Figure 13B:
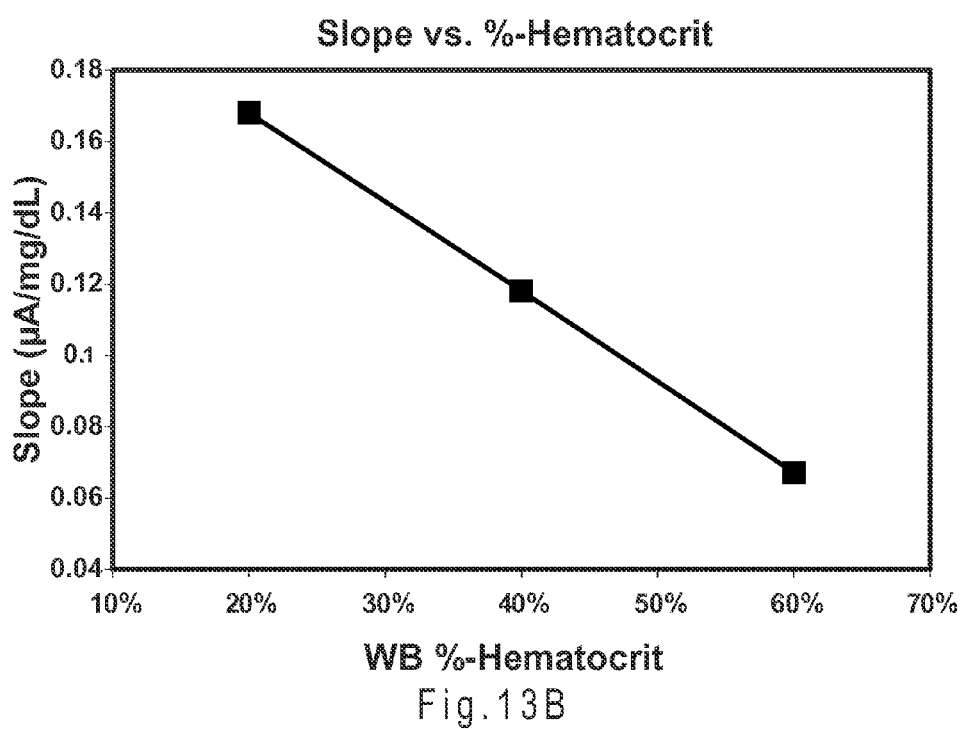
FIG. 13B shows the slope of calibration lines of current/glucose (µA/mg/dL) versus %-hematocrit derived from FIG. 11A.
Figure 14:
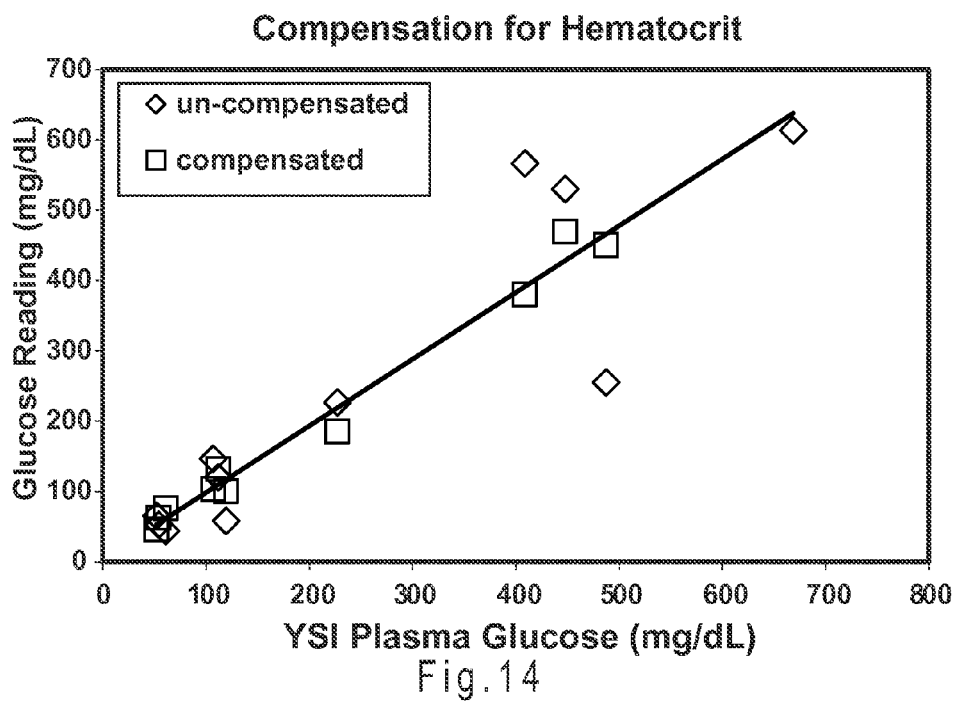
FIG. 14 illustrates the effect of correcting the glucose content (mg/dL) for hematocrit using the hematocrit index.

FIG. 13B depicts the correlation between slope and %-hematocrit for varying glucose concentrations at a fixed current with hematocrit compensation. As may be seen from the graph, the compensation equation determined to describe the curve of FIG. 13A provides a substantially linear correlation between current and glucose concentration, regardless of the underlying hematocrit content of the WB sample. FIG. 14 compares multiple compensated and un-compensated glucose readings obtained from a sensor system of the present invention with the values obtained from the YSI reference instrument.

The following examples are provided to illustrate one or more preferred embodiments of the invention. Numerous variations can be made to the following examples that lie within the scope of the invention.

EXAMPLES

Example 1

Preparation of the Sensor Strip

Figure 1B:
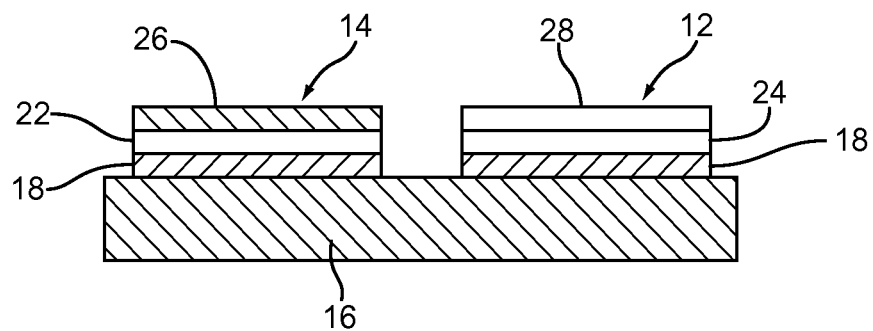

Referring to FIGS. 1A-B, electrodes 12 and 14 were formed on a base of insulating material, such as using the techniques described in U.S. Pat. Nos. 5,798,031 and 5,120,420, to prepare an electrochemical sensor strip 10. Silver paste 18 was deposited by screen printing onto a polycarbonate strip 16. This paste was printed in a pattern to form the electrical contacts 20a and 20b and the lower layer 18 of the electrodes 12 and 14.

Figure 2A:
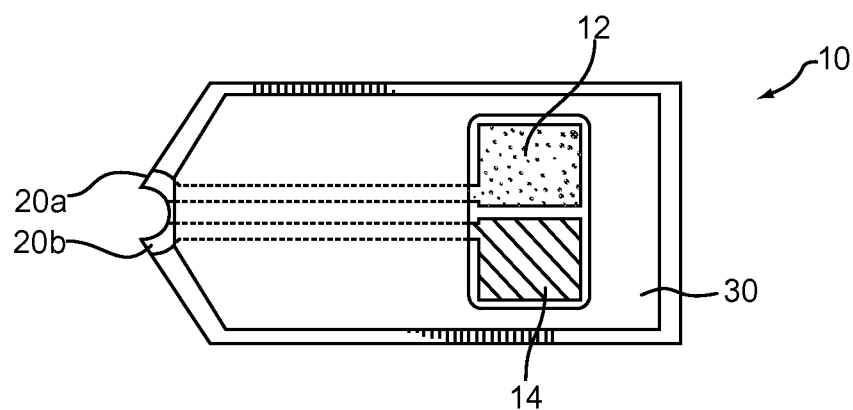
FIGS. 2A-2B represent exterior views of the sensor strip of FIGS. 1A-1B.

In FIG. 1B, an ink containing conductive carbon and a binder was then applied by screen printing in a pattern 22 and 24 to form the top layer of each electrode, a reagent layer 26 and 28 of glucose oxidase (or PQQ-GDH glucose dehydrogenase) and ferricyanide as a mediator. The working and counter electrodes 12 and 14 had surfaces of 1 mm and 1.2 mm$^2$, respectively, and the electrodes were separated by about 0.25 mm. In FIG. 2A, a dielectric layer 30 containing acrylate-modified polyurethane was deposited onto the base. The lower layers of the electrodes then were cured with UV radiation.

Figure 2B:
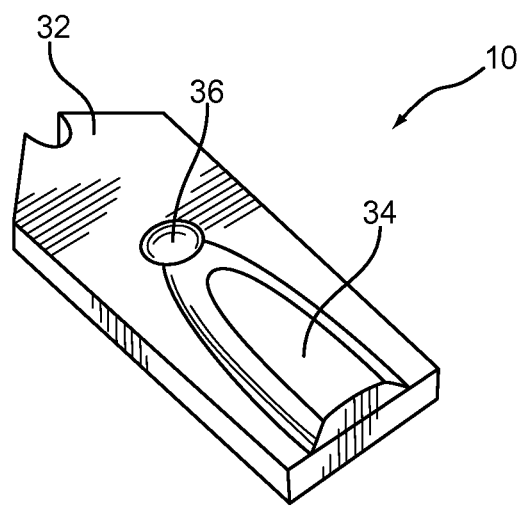

Referring to FIG. 2B, after drying, the base was bonded to a lid 32 to form the sensor strip 10. The construction of the lid was performed as described in U.S. Pat. No. 5,798,031. A coating solution of an aqueous polyurethane dispersion was spread on one side of a polycarbonate strip and allowed to dry. The strip was formed into a lid by embossing to form concave area 34 and by punching hole 36. The lid was bonded to the base by aligning and contacting the lid and the base, followed by applying heat to the contact area along the periphery of the structure.

The completed electrochemical sensor was activated using the procedures described in U.S. Pat. No. 5,429,735 to increase the activity of the electrode.

Example 2

Performing the Analysis

Figure 2C:
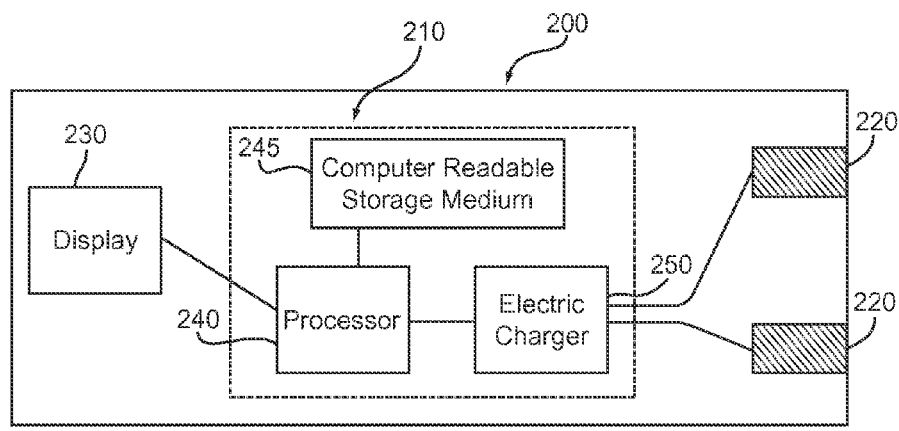
FIG. 2C is a schematic representation of a measuring device.

FIG. 2C is a schematic representation of a measuring device 200 including contacts 220 in electrical communication with electrical circuitry 210 and a display 230. In one aspect, the measuring device 200 is adapted to be handheld and to receive a sensor strip. In another aspect, the measuring device 200 is a handheld measuring device adapted to receive a sensor strip and implement voltammetric scanning. In another aspect, the measuring device 200 is a handheld measuring device adapted to receive a sensor strip and implement acyclic scanning.

The contacts 220 are adapted to provide electrical communication with the electrical circuitry 210 and the contacts of a sensor strip, such as the contacts 20a and 20b of the sensor strip 10 depicted in FIG. 1A. The electrical circuitry 210 may include an electric charger 250, a processor 240, and a computer readable storage medium 245. The electrical charger 250 may be a potentiostat or the like. Thus, the charger 250 may apply a voltage to the contacts 220 while recording the resulting current to function as a charger-recorder.

The processor 240 may be in electrical communication with the charger 250, the computer readable storage medium 245, and the display 230. If the charger is not adapted to record current, the processor 240 may be adapted to record the current at the contacts 220.

The computer readable storage medium 245 may be any storage medium, such as magnetic, optical, semiconductor memory, and the like. The computer readable storage medium 245 may be a fixed memory device or a removable memory device, such as a removable memory card. The display 230 may be analog or digital, in one aspect a LCD display adapted to displaying a numerical reading.

When the contacts of a sensor strip containing a sample are in electrical communication with the contacts 220, the processor 240 may direct the charger 250 to apply a voltammetric scan to the sample, thus starting the analysis. The processor 240 may start the analysis in response to the insertion of a sensor strip, the application of a sample to a previously inserted sensor strip, or in response to a user input, for example.

Instructions regarding implementation of the voltammetric scan may be provided by computer readable software code stored in the computer readable storage medium 245. The code may be object code or any other code describing or controlling the functionality described in this application. The data that results from the scan may be subjected to one or more data treatments in the processor 240 and the results, such analyte concentration, output to the display 230. As with the scanning instructions, the data treatment may be implemented by the processor 240 from computer readable software code stored in the computer readable storage medium 245.

Example 3

Cyclic Voltammetry and Semi-Integration

An 100 mg/dl aqueous glucose solution was introduced into an Ascensia AUTODISC® sensor. A cyclic scan having a 25 mV/sec scan rate was applied to the sensor strip using a CH Instrument potentiostat. The cyclic voltammogram (CV) was plotted as FIG. 3A, while its semi-integral (si) was plotted as FIG. 3B. The data was plotted as a function of the scanning potential vs. the potential at the counter electrode (ferricyanide). FIG. 3B further illustrates the plateau of the steady-state current in the semi-integral plot, where the difference between the steady-state plateau region between 0.2 V and 0.4 V, for example, was substantially zero, while the difference between the steady-state plateau and the forward current peak ($si_{ss}$) at ~0.15 V was relatively large.

The equations used for this semi-integral data treatment, and the derivative and semi-derivative data treatments described elsewhere, was implemented with the Electrochemical Workstation software package, version 4.07, revised Apr. 26, 2004, which accompanies the CH Instruments Electrochemical Workstation, model CHI 660A.

Example 4

Effect of Higher Glucose Concentration

In FIG. 5, cyclic scanning was applied to Ascensia AUTO-DISC® glucose sensor strips loaded with aqueous glucose solutions containing 0, 100, 200, 400 and 600 mg/dL glucose, labeled a-e, respectively. As seen in the FIG., the peak current for each glucose concentration rose and shifted to higher potentials as the glucose concentration increased. FIG. 6 depicts the corresponding semi-integrals for the cyclic voltammograms of FIG. 5. At zero glucose concentration, the semi-integral current was substantially zero.

Example 5

Cyclic Voltammetry of Glucose in WB Samples, Slow Scan

As generally described in the U.S. provisional patent application filed on Oct. 24, 2003, Ser. No. 60/513,817, sensor strips were constructed having different reagent layers on the working and counter electrodes. A layer of ferricyanide from a solution of about 22% $K_3Fe(CN)_6$, 0.7% bentone, 1.5% CMC, but without active ingredients, was deposited on the counter electrode. A layer was deposited on the working electrode made from a reagent solution of 16.8 unit/μL PQQ-GDH, 250 mM ferricyanide, 1.8% CMC, 64 mM phosphate and 64 mM NaCl. Whole blood samples containing 50 mg/dL glucose and 20%, 40%, or 60% hematocrit (labeled a-c, respectively in FIGS. 7A-7C) were introduced to the sensor strips.

The peak current from the 60% hematocrit sample (c) was the highest, but decayed the fastest to about the same steady-state current as the samples including 20% (a) and 40% (b) hematocrit. The current decay processes for 60% hematocrit whole blood samples the 50 mg/dL concentration is similar to that observed in FIGS. 7B and 7C for 100 and 400 mg/dL concentrations, respectively. As the glucose concentration increased in the 60% hematocrit whole blood samples, the steady-state current value decreased in relation to the current values obtained in 20% and 40% hematocrit samples.

Example 6

Semi-Integration of Cyclic Voltammograms

While cyclic and acyclic currents may be used directly to quantify the glucose concentrations of samples, the semi-integrals of these voltammograms provide preferable values to represent the glucose concentration of the sample. The semi-integrals presented in FIGS. 8A, 8B and 8C were obtained from FIGS. 7A, 7B, and 7C. Note the semi-integrals from the 20% whole blood samples (a) are substantially flat with virtually no peak at the plateau. As the hematocrit level increased, the peaks became more and more prominent from 40% to 60% hematocrit (b, c). Also as the glucose concentration increased, the three steady-state currents at 20%, 40% and 60% hematocrit separated further. The steady-state current at 0.3 V from the semi-integral was used to construct the calibration curves for the three hematocrits.

Example 7

Cyclic Voltammetry of Glucose in WB Samples, Fast Scan

The sensor strips described in Example 4 were used to conduct fast scan cyclic voltammetry with whole blood glucose at 20%, 40% and 60% hematocrit levels. FIGS. 9A, 9B, and 9C are cyclic voltammograms of whole blood including 400 mg/dL glucose at 0.025 V/sec, 0.5 V/sec and 1 V/sec scan rates, respectively. While a large displacement between the voltammetric currents at 0.3 V for voltammograms at the 0.025 V/sec scan rate existed, this displacement decreased with increased scan rates. Semi-integrals of these cyclic voltammograms are shown in FIGS. 10A, 10B, and 10C. The steady-state currents for each hematocrit percentage at the same glucose concentration merged together as the scan rate increased. The initial current peak was substantially reduced at fast scan rates.

Example 8

Acyclic Voltammetry of Glucose in WB Samples, Fast, Short Scan

Whole blood samples containing 400 mg/dL glucose and 20, 40, or 55% hematocrit were each applied to 3 sensor strips. After an approximate 6 second wait, a fast, 1 V/sec acyclic scan was applied from 0.2 V to 0.3 V and back to 0.2 V. After determining the semi-integral currents from the scans, as previously described with respect to FIG. 3H, the acyclic scan current value and the corresponding semi-integral current value at 0.3 V were used to determine the glucose concentration in each of the 3 WB samples.

Figure 17A:
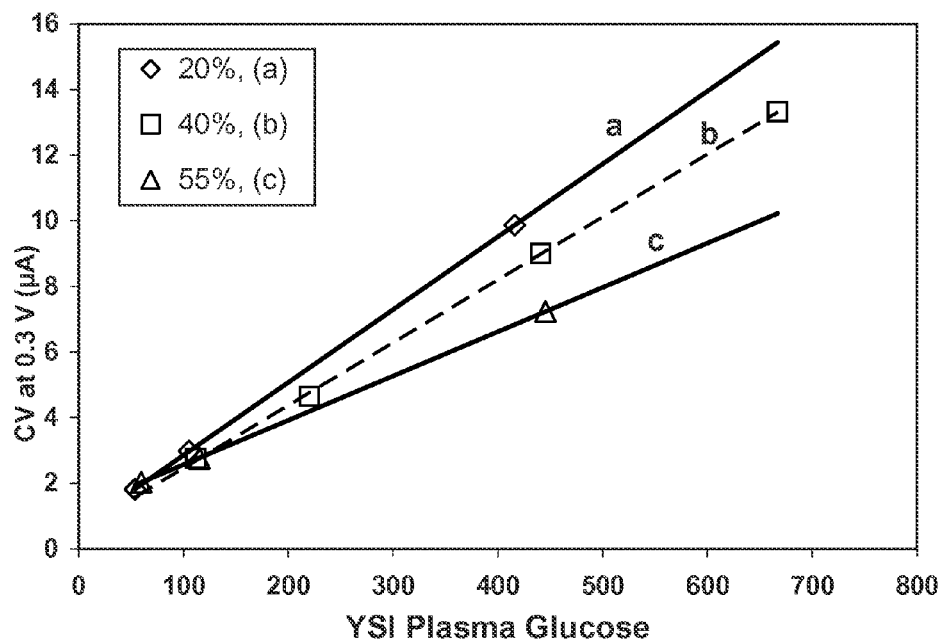
FIGS. 17A-17B show the dose response plots for recorded and semi-integral current values, respectively, of an acyclic scan.
Figure 17B:
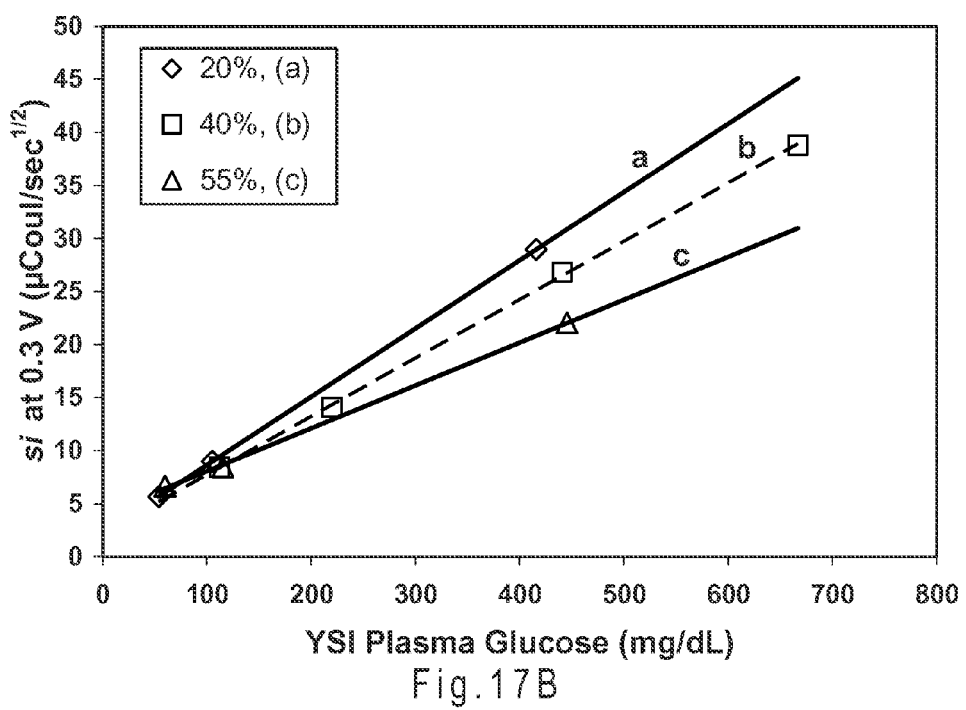
Figure 17C:
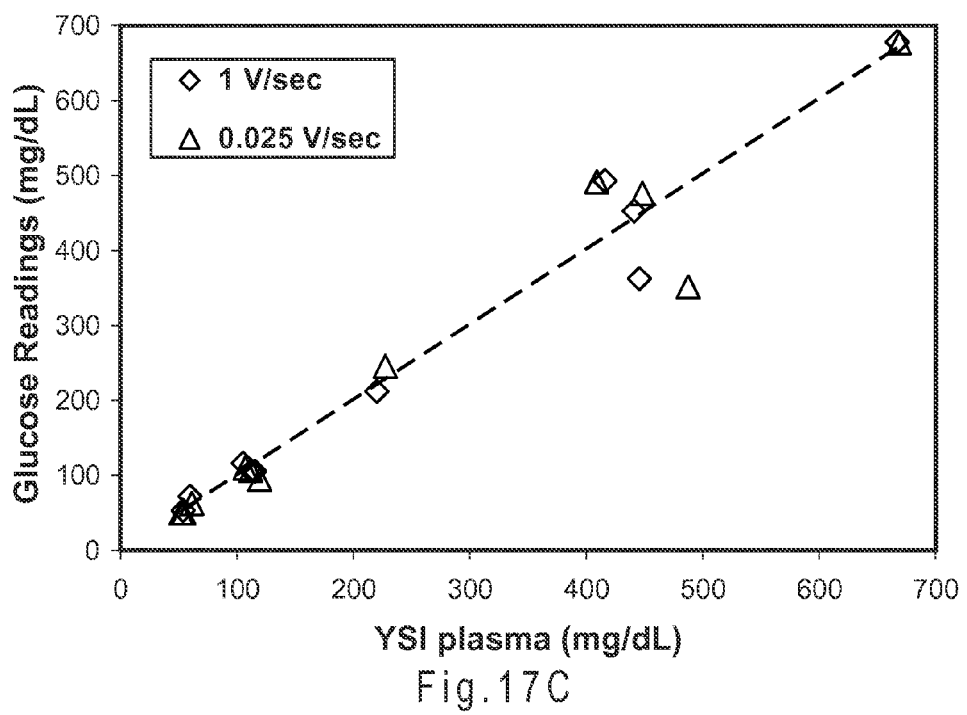
FIG. 17C compares the accuracy of the glucose concentration values obtained from the acyclic scan to a cyclic scan having a slow scan rate.

FIGS. 17A-17B show the dose response plots for the recorded current and semi-integral current values, respectively. In relation to the recorded current values, the semi-integral data treatment of FIG. 17B provided a slight reduction in analytical bias between the 20 and 55% samples attributable to the hematocrit effect. FIG. 17C compares the accuracy of the glucose concentration values obtained from the acyclic scan to those obtained from a cyclic scan having a slow scan rate of 0.025 V/sec. The concentration values obtained from the acyclic scan are closer to those obtained from the reference YSI instrument than those from the longer cyclic scan.

Example 9

Calibration Curves of si Currents at Different Scan Rates

Using the semi-integral currents from the 20%, 40%, and 60% hematocrit lines, calibration curves were constructed for scan rates of 0.025 V/sec, 0.5 V/sec and 1 V/sec, as shown in FIGS. 11A, 11B and 11C. The sensor strips were similar to those of Example 4. At a scan rate of 0.025 V/sec, three distinct lines were observed for the three hematocrits of whole blood samples tested in FIG. 11A. As the scan rate increased from 0.025 V/sec to 0.5 V/sec (FIG. 11B), the three calibration lines moved closer together and almost merged at 1 V/sec (FIG. 11C). This example demonstrated that glucose measurements in whole blood samples may avoid the hematocrit effect of the WB samples.

Example 10

Defining Hematocrit Index from Semi-Integrals

Figure 8A:
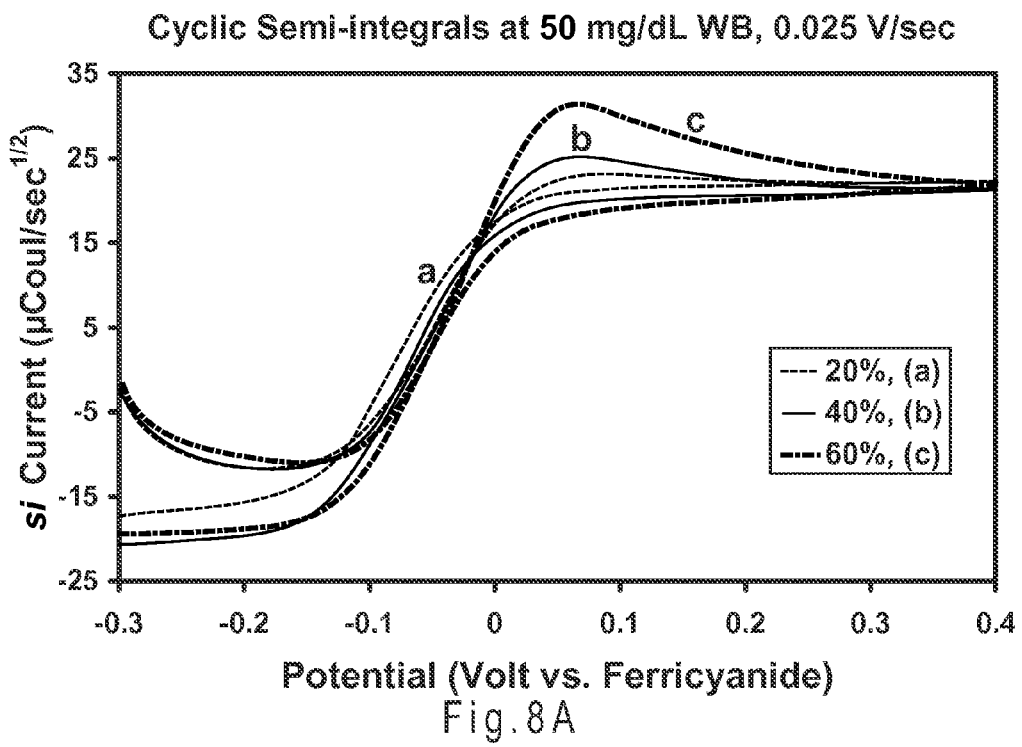
FIGS. 8A-C show the semi-integral currents of FIGS. 7A-7C.
Figure 8B:
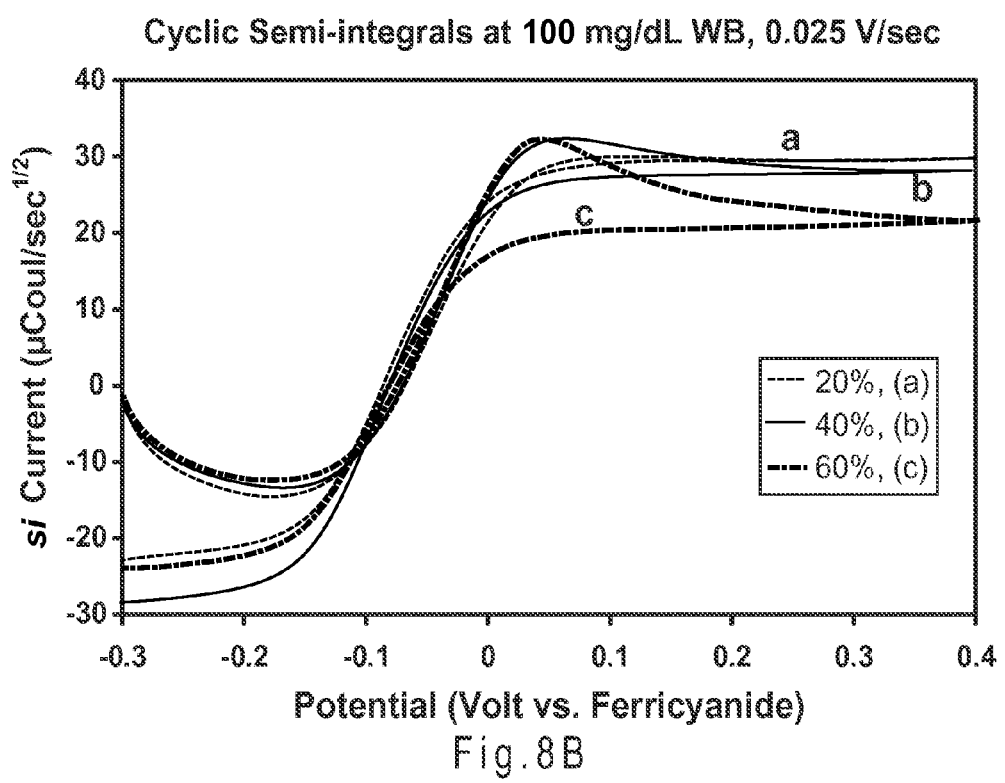
Figure 8C:
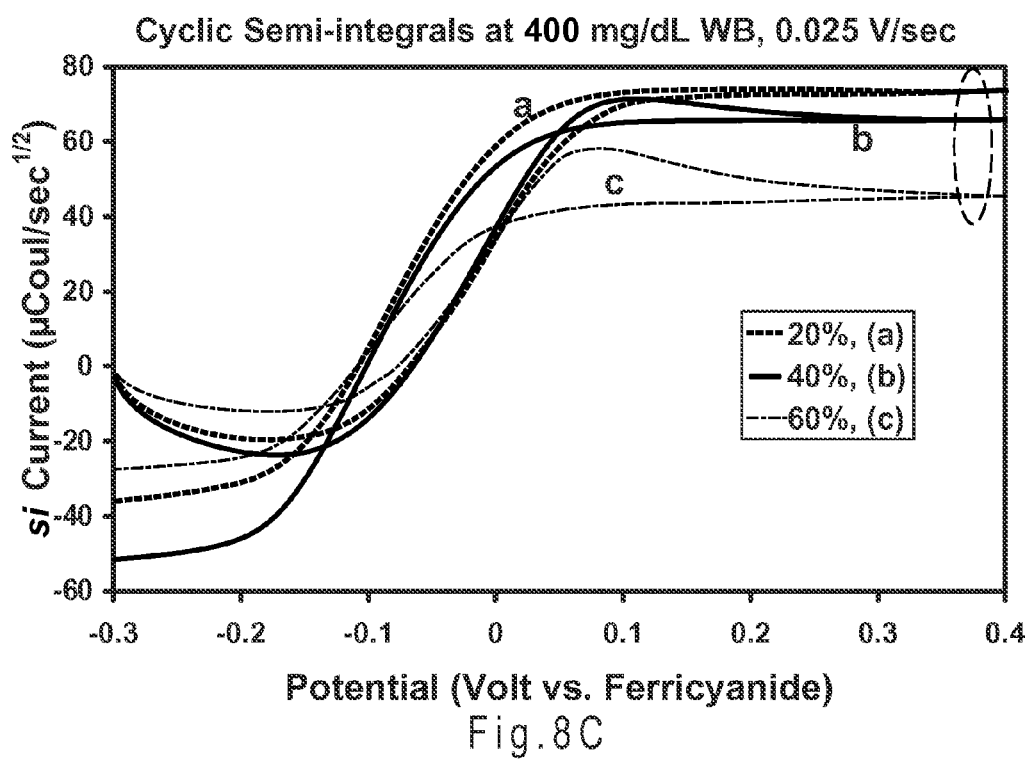
Figure 8D:
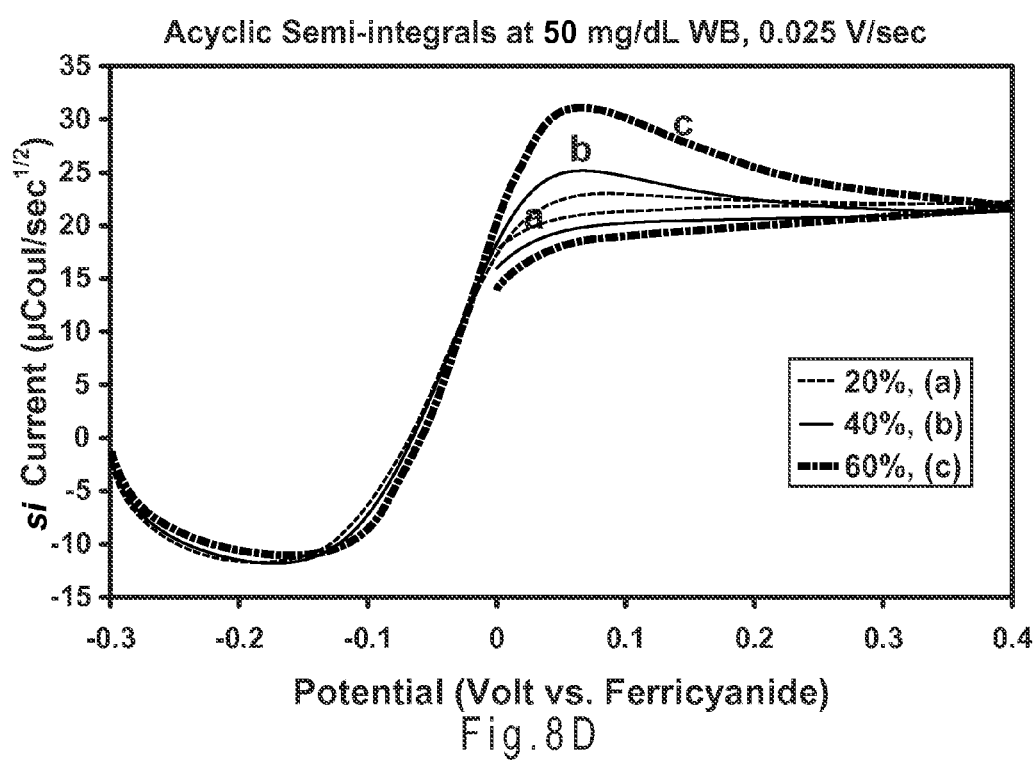
FIGS. 8D-8F show the semi-integral currents of FIGS. 7D-7F.
Figure 8E:
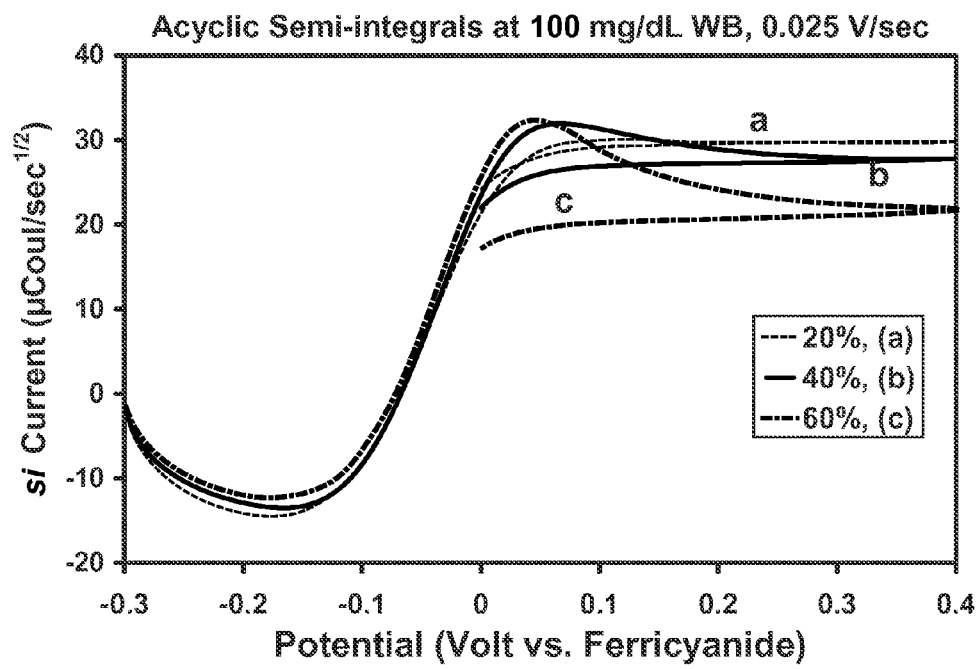
Figure 8F:
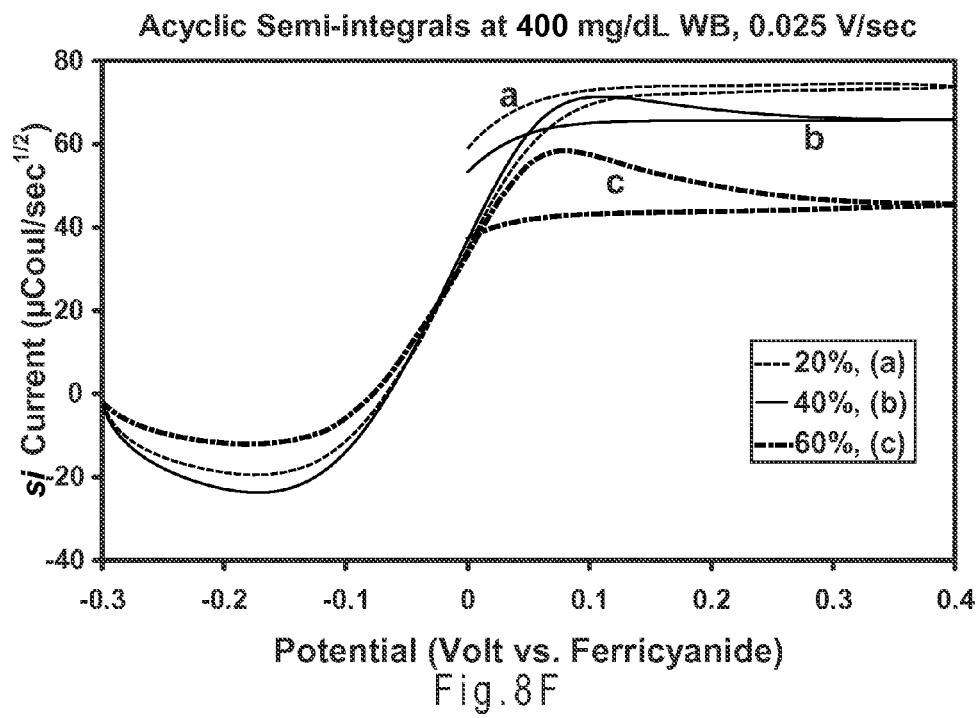

From FIGS. 8A-C, a relationship exists between the hematocrit level and the height of the current peaks. The ratio of peak height to steady-state current (si) is independent of the glucose concentration. This characteristic may be used to indicate the hematocrit level in the whole blood sample.

FIG. 12 defines the Hematocrit Index (HI) as the ratio of the peak current to the steady-state current from the semi-integral. The table below lists the peak and plateau currents of semi-integrals at 50, 100, and 400 mg/dL whole blood glucose and 20%, 40%, and 60% hematocrit.

|  | Peak and Plateau Currents (si): | | | | | |
| --- | --- | --- | --- | --- | --- | --- |
| WB glucose | 20% | | 40% | | 60% | |
| mg/dL | Peak | plateau | Peak | plateau | Peak | plateau |
| 50 | 34.69 | 34.31 | 36.94 | 32.79 | 42.25 | 31.74 |
| 100 | 44.4 | 43.88 | 45.22 | 40.76 | 44.58 | 33.44 |
| 400 | 92.34 | 93.46 | 94.74 | 89.16 | 70.74 | 56.71 |

|  | Hematocrit Index (HI): Peak/Plateau Ratio | | |
| --- | --- | --- | --- |
|  | 20% | 40% | 60% |
| 50 | 1.01 | 1.13 | 1.33 |
| 100 | 1.01 | 1.11 | 1.33 |
| 400 | 0.99 | 1.06 | 1.25 |
| Ave | 1.00 | 1.10 | 1.30 |
| StdDev | 0.014 | 0.033 | 0.049 |
| %-CV | 1.35 | 3.01 | 3.75 |

Example 11

Compensation of Measurement Biases for WB Glucose

The whole blood %-hematocrit was plotted against the hematocrit index (HI) value as a calibration curve for the hematocrit index, as shown in FIG. 13A. At the same time, the slope of the glucose calibration lines at the three hematocrit levels from FIG. 11A was plotted against the WB %-hematocrit, as shown in FIG. 13B. Instead of using the single slope (and intercept) at 40% hematocrit to calculate the glucose values from the current signals, %-hematocrit-dependent slope was used. This was accomplished in the following manner:
  (a) after the peak and plateau currents from a semi-integral, such as from FIG. 12 was obtained, the Hematocrit Index (HI) value was calculated.
  (b) Using this HI value, the %-hematocrit value of a WB sample was found from FIG. 13A.
  (c) Using this %-hematocrit value, an appropriate calibration slope was determined from FIG. 13B, which is hematocrit-dependent. A similar method also may be used to find the hematocrit-dependent intercept.
  (d) The slope (and intercept) from (c) was then used to convert the si current into a glucose value.

FIG. 14 shows the final result of such a compensation procedure, where uncompensated glucose readings are shown as diamonds, while compensated data points are shown as open squares. The improvement in accuracy is evident, particularly at higher glucose concentration.

Example 12

Derivatives of Cyclic Voltammograms

Figure 7A:
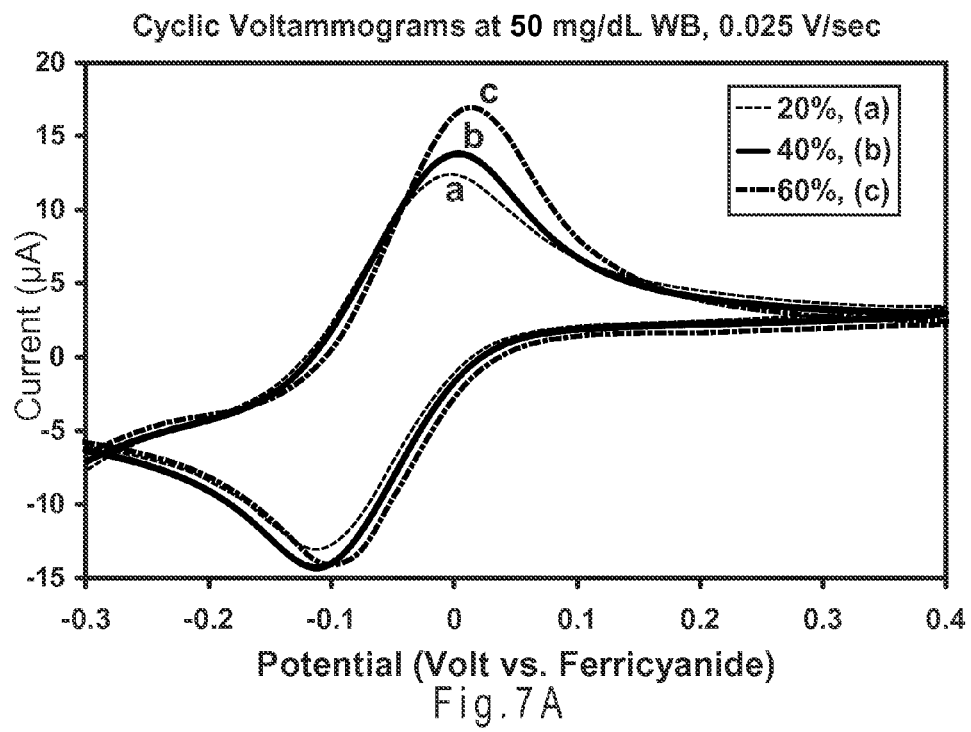
FIGS. 7A-7C are cyclic voltammograms illustrating the effect of variations in hematocrit percentage and glucose concentration in whole blood.
Figure 7B:
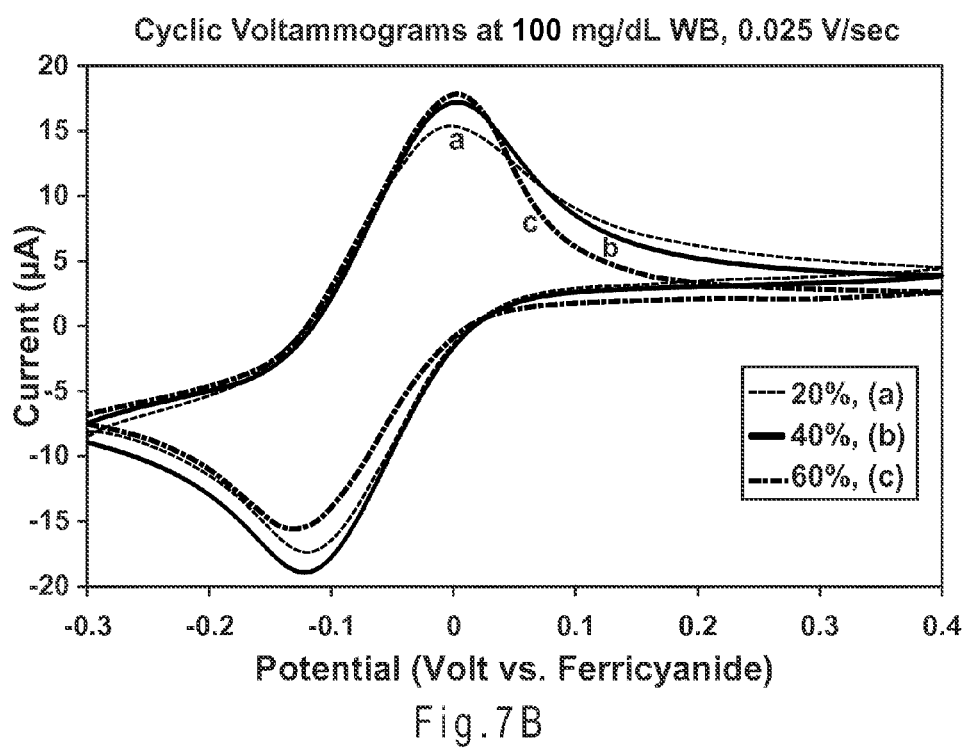
Figure 7C:
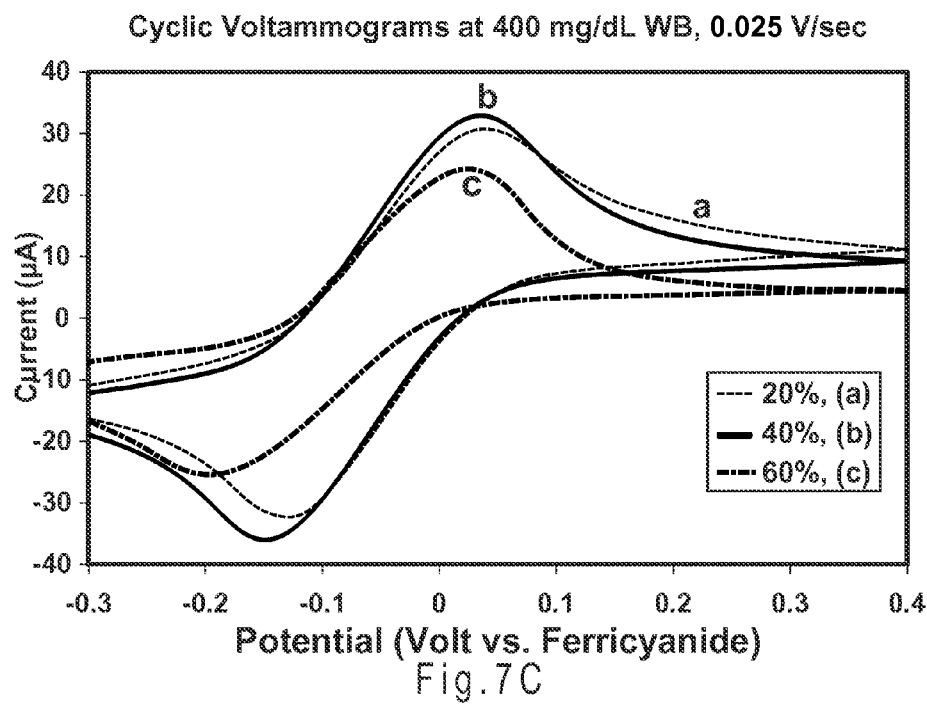
Figure 7D:
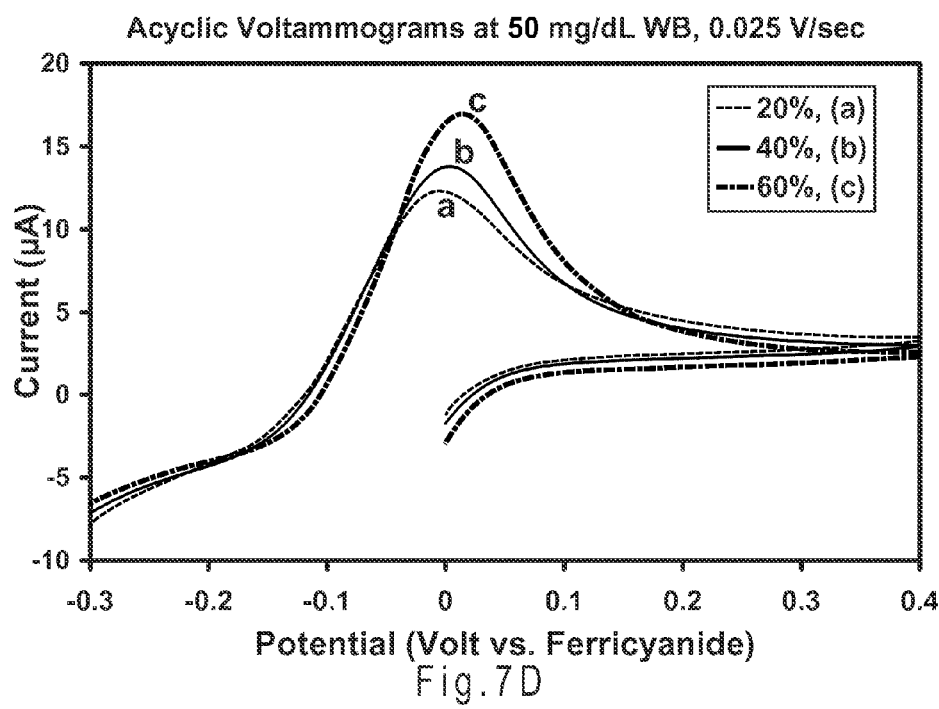
FIGS. 7D-7F are acyclic voltammograms illustrating the effect of variations in hematocrit percentage and glucose concentration in whole blood.
Figure 7E:
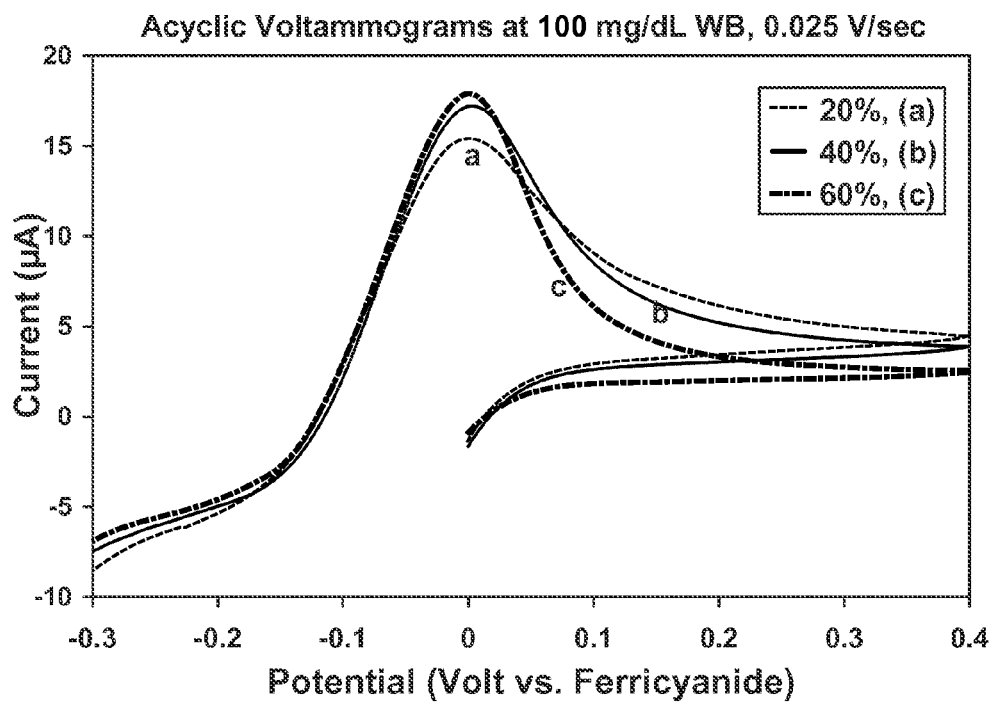
Figure 7F:
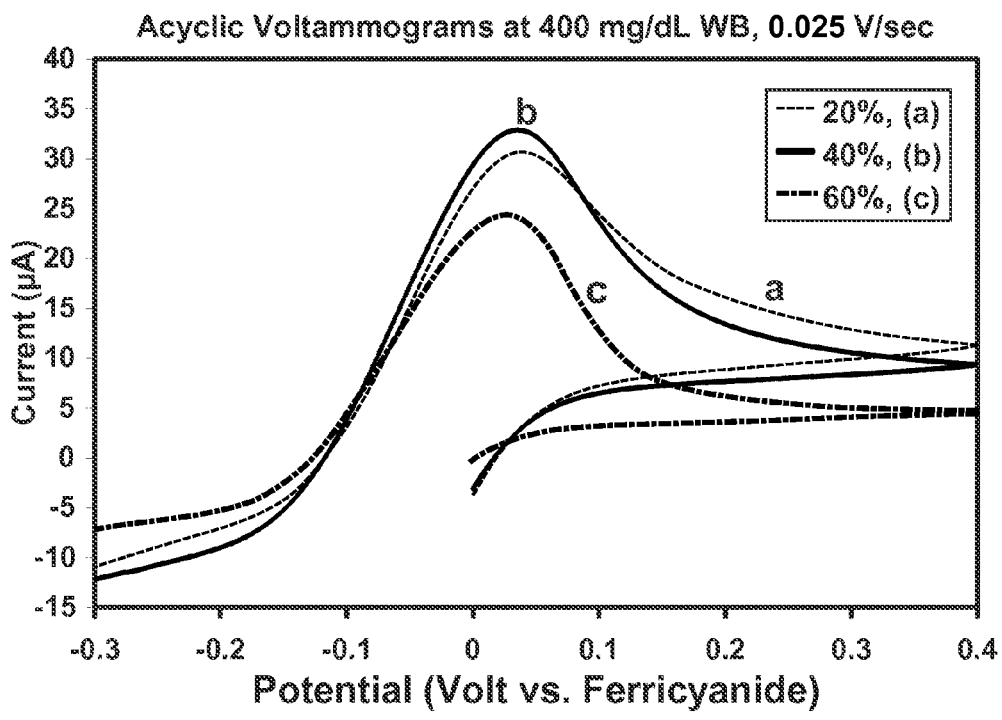

Hematocrit values may be distinguished by the current decay process that may follow the peak current in a scan. This feature is shown in FIGS. 7A, 7B, and 7C, where the current decay is the fastest in 60% hematocrit whole blood. This feature also may be represented by taking the derivative of the voltammetric currents from the scan. FIGS. 15A-15C show the derivatives of cyclic voltammograms at 50 mg/dL, 100 mg/dL, and 400 mg/dL, with 20%, 40%, and 60% hematocrit percentages. The largest negative peak in the derivative curve represents the fastest current decay of the cyclic voltammograms of FIGS. 7A-7C. Thus, the peak height in the derivative diagram may be used to compensate for the analytical bias due to the hematocrit effect in whole blood. In one aspect, the method illustrated in FIGS. 16A-16C was used, which is similar to that discussed in Example 9 for semi-integrated currents.

Figure 16A:
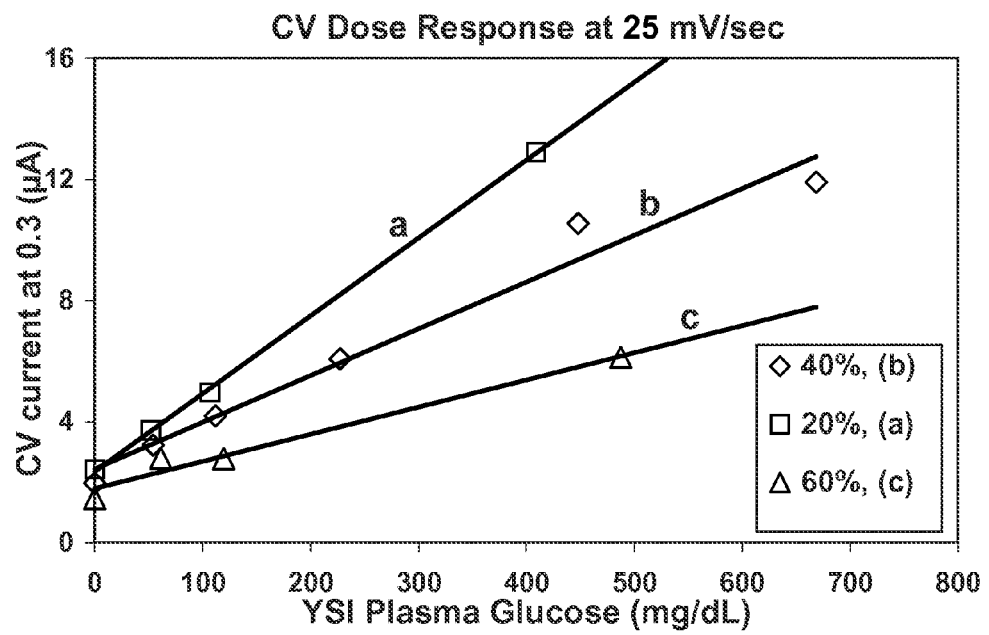
FIG. 16A plots the current at 0.3 volts versus % glucose at 20, 40, and 60% hematocrit.
Figure 16B:
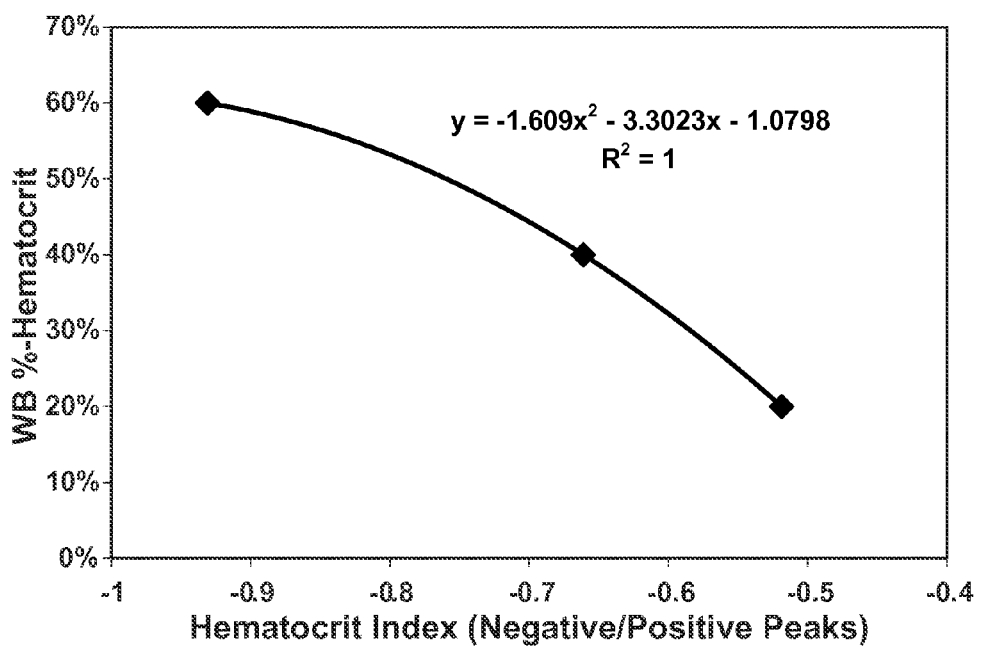
FIG. 16B plots the %-hematocrit versus the ratio of the negative and positive peaks illustrated in FIG. 15.
Figure 16C:
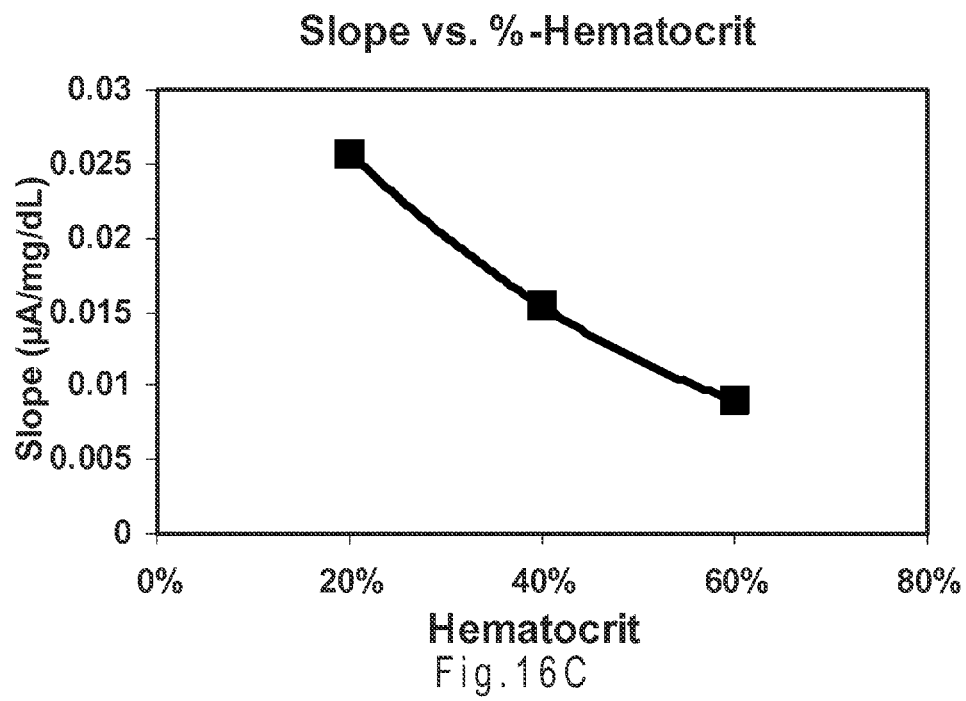
FIG. 16C plots the slope of the curves of FIG. 16A versus %-hematocrit.
Figure 16D:
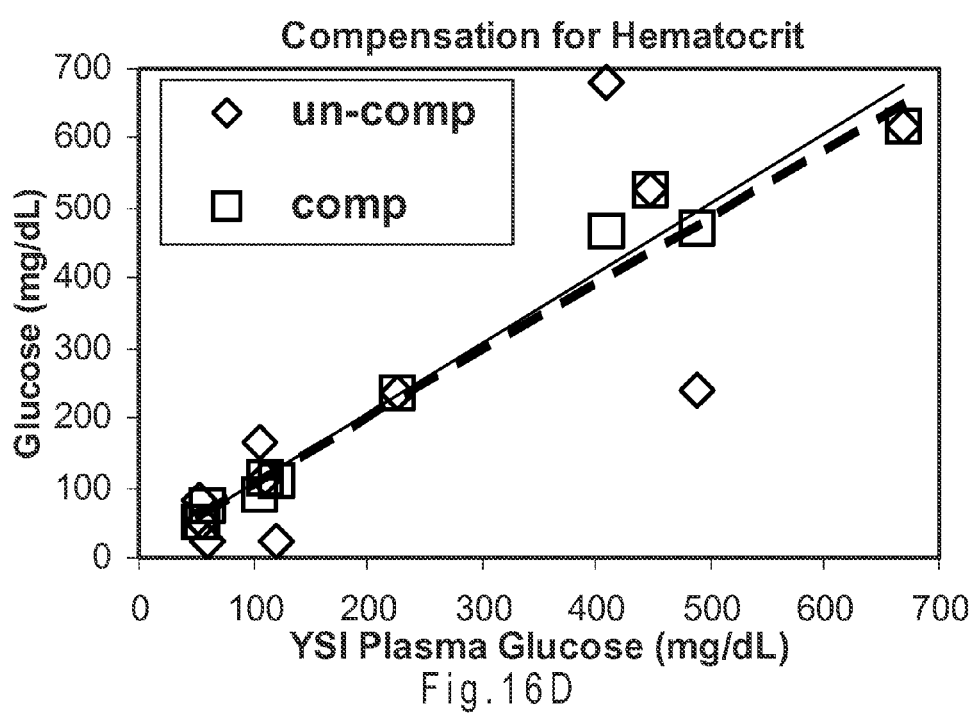
FIG. 16D shows the effect of correcting glucose content for hematocrit using derivative currents.

FIG. 16A shows a plot of CV currents at the steady-state region of 0.3 volts versus the % glucose at 20, 40, and 60% hematocrit. This is similar to FIG. 11A for semi-integrals and illustrates the divergence of the currents with increasing hematocrit. FIG. 16B shows a plot of the average ratio of the negative to positive peaks versus %-hematocrit of FIGS. 15A-15C. This ratio is another definition of a Hematocrit Index, in this case using derivatives of the current versus voltage rather than the semi-integral currents. FIG. 16C shows the slope of the curves of FIG. 16A versus %-hematocrit. In a similar procedure to that for semi-integration, derivatives of current versus voltage were obtained and the negative to positive peaks were used to define a Hematocrit Index (HI-DER). The HI-DER was used to determine the %-hematocrit from FIG. 16B. Then, FIG. 16C was used to correct the measured glucose content for the %-hematocrit. FIG. 16D showed the correction for the hematocrit effect using the derivatives of currents obtained by voltammetry.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:
1. A method of determining the concentration of an analyte in a sample, comprising:
  oxidizing or reducing the analyte,
  applying a voltammetric forward linear scan to the sample, where the forward linear scan applies a changing voltage, and
  the sample comprises at least one species of a redox pair;
  measuring current as a function of the changing voltage;
  applying a data treatment to the measured current; and
  determining a concentration of an analyte in the sample in response to the data treatment.
2. The method of claim 1, where the analyte is selected from the group consisting of glucose, cholesterol, triglycerides, lactate, pyruvate, alcohol, bilirubin, uric acid, NAD(P)H, and carbon monoxide.

3. The method of claim 2, where the sample comprises blood.

4. The method of claim 1, further comprising applying a voltammetric reverse linear scan to the sample at a reversing point of the forward linear scan.

5. The method of claim 4, where the voltammetric forward and reverse linear scans comprise an acyclic scan.

6. The method of claim 4, where the voltammetric forward and reverse linear scans comprise a cyclic scan.

7. The method of claim 4, where the reverse scan comprises at least 25 mV of steady-state region.

8. The method of claim 7, where the steady-state region of the scan comprises a change in electrochemical current with respect to voltage of at most ±10%.

9. The method of claim 4, where the reversing point is selected to provide from 25 to 400 mV of steady-state region.

10. The method of claim 1, further comprising changing the voltage of the forward scan at a rate of at least 176 mV/second.

11. The method of claim 10, further comprising changing the voltage of the forward scan at a rate of at least 500 mV/second.

12. The method of claim 1, where the forward scan comprises a scan range from 400 to 1000 mV.

13. The method of claim 1, where the forward scan comprises at least one voltage providing at least a 100:1 concentration ratio between two species of a redox pair.

14. The method of claim 1, where the forward scan comprises at least one potential at a working electrode of at least 180 mV.

15. The method of claim 1, where the data treatment is selected from the group consisting of a semi-integral data treatment, a derivative data treatment, a semi-derivative data treatment, and combinations thereof.

16. The method of claim 1, where the data treatment comprises a semi-integral data treatment.

17. The method of claim 16, where the applying the data treatment comprises semi-integrating the currents from the forward linear scan and determining a steady-state semi-integral current.

18. The method of claim 16, where the semi-integral data treatment separates at least one steady-state current from at least one hematocrit-affected equilibrium current.

19. The method of claim 16, where the semi-integral data treatment comprises at least one half-step integration.

20. The method of claim 16, where the semi-integral data treatment lacks a time-dependence factor.

21. The method of claim 16, further comprising determining a ratio of a peak current value to a steady-state current value in response to a hematocrit compensation.

22. The method of claim 1, where the data treatment comprises a semi-derivative data treatment.

23. The method of claim 22, where the semi-derivative data treatment transforms at least a portion of a voltammetric current region into a peak.

24. The method of claim 1, where the data treatment comprises a derivative data treatment.

25. The method of claim 24, where the derivative data treatment comprises hematocrit compensation comprising dividing a negative peak by a positive peak.

26. The method of claim 1, where the determining comprises hematocrit compensation.

27. The method of claim 26, where the hematocrit compensation comprises determining a ratio of a peak current value to a steady-state current value.

28. The method of claim 1, where the determining comprises inputting at least one steady-state current value into a compensation equation.

29. The method of claim 1, where the determined concentration of the analyte in the sample provides a concentration value closer to that obtained from a reference instrument than if coulometry were substituted for the voltammetric forward linear scan.

* * * * *